US010835507B2

(12) United States Patent
Chandraratna et al.

(10) Patent No.: US 10,835,507 B2
(45) Date of Patent: Nov. 17, 2020

(54) TREATMENT OF MUSCULAR DISORDERS WITH COMBINATIONS OF RXR AGONISTS AND THYROID HORMONES

(71) Applicant: Io Therapeutics, Inc., Santa Ana, CA (US)

(72) Inventors: Roshantha A. Chandraratna, San Juan Capistrano, CA (US); Martin E. Sanders, Seattle, WA (US)

(73) Assignee: Io Therapeutics, Inc., Houston, TX (US)

(*) Notice: Subject to any disclaimer, the term of this patent is extended or adjusted under 35 U.S.C. 154(b) by 0 days.

(21) Appl. No.: 16/083,619

(22) PCT Filed: Oct. 31, 2016

(86) PCT No.: PCT/US2016/059775
§ 371 (c)(1),
(2) Date: Sep. 10, 2018

(87) PCT Pub. No.: WO2017/155578
PCT Pub. Date: Sep. 14, 2017

(65) Prior Publication Data
US 2019/0298678 A1    Oct. 3, 2019

Related U.S. Application Data

(60) Provisional application No. 62/306,472, filed on Mar. 10, 2016.

(51) Int. Cl.
| | |
|---|---|
| *A61K 31/201* | (2006.01) |
| *A61K 31/44* | (2006.01) |
| *A61K 31/192* | (2006.01) |
| *A61K 31/198* | (2006.01) |
| *A61P 25/16* | (2006.01) |
| *A61K 31/4418* | (2006.01) |
| *A61K 31/216* | (2006.01) |
| *A61P 21/00* | (2006.01) |
| *A61P 9/10* | (2006.01) |
| *A61K 45/06* | (2006.01) |

(52) U.S. Cl.
CPC .......... *A61K 31/201* (2013.01); *A61K 31/192* (2013.01); *A61K 31/198* (2013.01); *A61K 31/216* (2013.01); *A61K 31/44* (2013.01); *A61K 31/4418* (2013.01); *A61P 9/10* (2018.01); *A61P 21/00* (2018.01); *A61P 25/16* (2018.01); *A61K 45/06* (2013.01)

(58) Field of Classification Search
CPC .............. A61K 31/198; A61K 31/4418; A61K 31/192; A61K 31/216; A61K 31/44; A61K 2300/00; A61K 31/201; A61K 45/06; A61P 21/00; A61P 25/16; A61P 9/10
See application file for complete search history.

(56) References Cited

U.S. PATENT DOCUMENTS

| | | |
|---|---|---|
| 4,756,911 A | 7/1988 | Drost |
| 5,378,475 A | 1/1995 | Smith |
| 5,455,265 A | 10/1995 | Chandraratna |
| 5,466,861 A | 11/1995 | Dawson et al. |
| 5,663,367 A | 9/1997 | Vuligonda et al. |
| 5,675,033 A | 10/1997 | Vuligonda et al. |
| 5,728,846 A | 3/1998 | Vuligonda et al. |
| 5,739,338 A | 4/1998 | Beard et al. |
| 5,763,635 A | 6/1998 | Vuligonda et al. |
| 5,773,594 A | 6/1998 | Johnson et al. |
| 5,776,699 A | 7/1998 | Klein et al. |
| 5,780,647 A | 7/1998 | Vuligonda et al. |
| 5,817,836 A | 10/1998 | Vuligonda et al. |
| 5,856,490 A | 1/1999 | Teng |
| 5,877,207 A | 3/1999 | Klein et al. |
| 5,917,082 A | 6/1999 | Vuligonda et al. |
| 5,919,970 A | 7/1999 | Song et al. |
| 5,952,345 A | 9/1999 | Klein et al. |
| 5,958,954 A | 9/1999 | Klein et al. |
| 5,965,606 A | 10/1999 | Teng |
| 5,998,655 A | 12/1999 | Vuligonda et al. |
| 6,008,204 A | 12/1999 | Klein et al. |
| 6,048,873 A | 1/2000 | Vasudevan et al. |
| 6,034,242 A | 3/2000 | Vuligonda et al. |
| 6,037,488 A | 3/2000 | Song et al. |
| 6,043,381 A | 3/2000 | Vuligonda et al. |
| 6,063,768 A | 5/2000 | First |
| 6,087,505 A | 7/2000 | Vuligonda et al. |
| 6,090,810 A | 7/2000 | Klein et al. |
| 6,114,533 A | 9/2000 | Vuligonda et al. |

(Continued)

FOREIGN PATENT DOCUMENTS

| | | |
|---|---|---|
| EP | 25556827 A1 | 2/2013 |
| JP | 2010-280585 A | 12/2010 |

(Continued)

OTHER PUBLICATIONS

Assaf et al., Minimizing adverse side-effects of oral bexarotene in cutaneous T-cell lymphoma: an expert opinion. British Journal of Dermatology, 155, pp. 261-266 (2006).

Diab et al., Ligands for the peroxisome proliferator-activated receptor-gamma and the retinoid X receptor exert additive anti-inflammatory effects on experimental autoimmune encephalomyelitis. Journal of Neuroimmunology, 148, pp. 116-126 (2004).

Liu et al., Mechanism of selective retinoid X receptor agonist-induced hypothroidism in the rat. Endocrinology, 143 (8):2880-2885 (2002).

(Continued)

*Primary Examiner* — Kortney L. Klinkel
*Assistant Examiner* — William Y Lee
(74) *Attorney, Agent, or Firm* — K&L Gates LLP; Louis C. Cullman; David Diamond

(57) ABSTRACT

The present specification provides methods of treating a muscular disorder with a combination of a RXR agonist and a thyroid hormone.

15 Claims, 11 Drawing Sheets

(56) References Cited

U.S. PATENT DOCUMENTS

| | | |
|---|---|---|
| 6,117,987 A | 9/2000 | Johnson et al. |
| 6,147,224 A | 11/2000 | Vuligonda et al. |
| 6,187,750 B1 | 2/2001 | Chein |
| 6,211,385 B1 | 4/2001 | Vuligonda et al. |
| 6,218,128 B1 | 4/2001 | Klein et al. |
| 6,225,494 B1 | 5/2001 | Song et al. |
| 6,228,848 B1 | 5/2001 | Klein et al. |
| 6,235,923 B1 | 5/2001 | Song et al. |
| 6,313,163 B1 | 11/2001 | Vuligonda et al. |
| 6,313,168 B1 | 11/2001 | Pacifici et al. |
| 6,387,950 B2 | 5/2002 | Nehme |
| 6,403,638 B1 | 6/2002 | Vuligonda et al. |
| 6,521,624 B1 | 2/2003 | Klein et al. |
| 6,521,641 B1 | 2/2003 | Klein et al. |
| 6,538,149 B1 | 3/2003 | Vuligonda et al. |
| 6,555,690 B2 | 4/2003 | Johnson et al. |
| 6,610,744 B2 | 8/2003 | Teng et al. |
| 6,630,463 B2 | 10/2003 | Kikuchi et al. |
| 6,653,483 B1 | 11/2003 | Johnson et al. |
| 6,720,423 B2 | 4/2004 | Vasudevan et al. |
| 6,720,425 B2 | 4/2004 | Johnson et al. |
| 6,776,984 B1 | 8/2004 | Schwartz |
| 6,818,775 B2 | 11/2004 | Johnson et al. |
| 6,942,980 B1 | 9/2005 | Klein et al. |
| 7,048,946 B1 | 5/2006 | Wong |
| 7,105,566 B2 | 9/2006 | Chandraratna et al. |
| 7,166,726 B2 | 1/2007 | Vuligonda et al. |
| 8,101,662 B2 | 1/2012 | Chandraratna |
| 9,308,186 B2 | 4/2016 | Chandraratna |
| 9,655,872 B2 | 5/2017 | Chandraratna |
| 9,717,702 B2 | 8/2017 | Chandraratna |
| 9,877,941 B2 * | 1/2018 | Chandraratna ......... A61P 25/16 |
| 10,039,731 B2 | 8/2018 | Chandraratna |
| 10,092,535 B2 * | 10/2018 | Chandraratna ......... A61P 25/16 |
| 10,188,618 B2 | 1/2019 | Chandraratna |
| 10,201,512 B2 | 2/2019 | Chandraratna |
| 2001/0037025 A1 | 11/2001 | Murray et al. |
| 2002/0156054 A1 | 10/2002 | Klein et al. |
| 2002/0173631 A1 | 11/2002 | Johnson et al. |
| 2002/0193403 A1 | 12/2002 | Yuan et al. |
| 2003/0013766 A1 | 1/2003 | Lamph et al. |
| 2003/0077664 A1 | 4/2003 | Zhao et al. |
| 2003/0144330 A1 | 7/2003 | Spiegelman |
| 2003/0219832 A1 | 11/2003 | Klein et al. |
| 2004/0049072 A1 | 3/2004 | Ardecky |
| 2004/0147611 A1 | 7/2004 | Yuan et al. |
| 2004/0037025 A1 | 11/2004 | Murray et al. |
| 2005/0004213 A1 | 1/2005 | Sinha et al. |
| 2005/0171151 A1 | 8/2005 | Yuan et al. |
| 2005/0181017 A1 | 8/2005 | Hughes |
| 2005/0244464 A1 | 11/2005 | Hughes |
| 2006/0286127 A1 | 12/2006 | Van Schaack et al. |
| 2007/0054882 A1 | 3/2007 | Klein et al. |
| 2007/0077652 A1 | 4/2007 | Peled et al. |
| 2007/0078129 A1 | 4/2007 | Lagu et al. |
| 2007/0122476 A1 | 5/2007 | Hanshew |
| 2007/0185055 A1 | 8/2007 | Jiang |
| 2007/0265449 A1 | 11/2007 | Vuligonda et al. |
| 2009/0004291 A1 | 1/2009 | Song |
| 2009/0136470 A1 | 5/2009 | Hilde et al. |
| 2009/0203720 A1 | 8/2009 | Zhao et al. |
| 2009/0227674 A1 | 9/2009 | Richon |
| 2010/0298434 A1 | 11/2010 | Rouillard |
| 2011/0008437 A1 | 1/2011 | Altman |
| 2012/0115912 A1 | 5/2012 | Landreth |
| 2012/0238623 A1 | 9/2012 | Chandraratna |
| 2013/0190395 A1 | 7/2013 | Chandraratna et al. |
| 2014/0235676 A1 | 8/2014 | Landreth |
| 2014/0286973 A1 | 9/2014 | Powell, Jr. |
| 2015/0038585 A1 | 2/2015 | Chandraratna |
| 2015/0196517 A1 | 7/2015 | Chandraratna et al. |
| 2015/0342917 A1 | 12/2015 | Chandraratna et al. |
| 2017/0056348 A1 | 3/2017 | Chandraratna et al. |
| 2017/0119713 A1 | 5/2017 | Chandraratna et al. |
| 2017/0119714 A1 | 5/2017 | Chandraratna et al. |
| 2018/0064670 A1 | 3/2018 | Chandraratna et al. |
| 2018/0116985 A1 | 5/2018 | Chandraratna |
| 2018/0263939 A1 | 9/2018 | Chandraratna et al. |
| 2018/0318241 A1 | 11/2018 | Chandraratna et al. |
| 2018/0369181 A1 | 12/2018 | Chandraratna et al. |
| 2019/0083441 A1 | 3/2019 | Chandraratna et al. |

FOREIGN PATENT DOCUMENTS

| | | |
|---|---|---|
| WO | 1994/012880 A2 | 6/1994 |
| WO | 1994/014777 | 7/1994 |
| WO | 1996/039374 A1 | 12/1996 |
| WO | 1997/009297 A2 | 3/1997 |
| WO | 1999/008992 A1 | 2/1999 |
| WO | 1999/033821 A1 | 7/1999 |
| WO | 1999/063980 A1 | 12/1999 |
| WO | 2000/020370 A1 | 4/2000 |
| WO | 2001/007028 A2 | 2/2001 |
| WO | 2002/089781 A2 | 11/2002 |
| WO | 2002/089842 | 11/2002 |
| WO | 2003/027090 A2 | 4/2003 |
| WO | 2003/062369 | 7/2003 |
| WO | 2003/078567 | 9/2003 |
| WO | 2003/093257 A1 | 11/2003 |
| WO | 2003/101928 | 12/2003 |
| WO | 2004/046096 | 6/2004 |
| WO | 2007/041076 A2 | 4/2007 |
| WO | 2007/041398 | 4/2007 |
| WO | 2008/157394 A2 | 12/2008 |
| WO | 2010/132671 A1 | 11/2010 |
| WO | 2011/006157 A2 | 1/2011 |
| WO | 2013/020966 | 2/2013 |
| WO | 2013/090616 A1 | 6/2013 |
| WO | 2015/059632 A1 | 4/2015 |
| WO | 2016/144976 A1 | 9/2016 |
| WO | 2017/075610 | 5/2017 |
| WO | 2017/075612 A1 | 5/2017 |
| WO | 2017/155577 A1 | 9/2017 |
| WO | 2017/155578 A1 | 9/2017 |
| WO | 2019/046591 A1 | 3/2019 |

OTHER PUBLICATIONS

Supplementary European Search Report for European Patent Application Serial No. 16861057 dated May 22, 2019.

Vuligonda et al., Enantioselective syntheses of potent retinoid X receptor ligands: Differential biological activities of individual antipodes. J. Med. Chem., 44. pp. 2298-2303 (2001).

Farmer et al., Retinoic acid receptor ligands based on the 6-cyclopropyl-2,4-hexadienoic acid. Bioorganic & Medicinal Chemistry Letters, 13:261-264 (2003).

Koivusalo et al., The cytotoxicity of chemotherapy drugs varies in cervical cancer cells depending on the p53 status. Cancer Biology and Therapy, vol. 3278(11):1177-1183 (2004).

Inoue et al., Rexinoids isolated from Sophora tonkinensis with a gene expression profile distinct from the synthetic rexinoid bexarotene. J. Nat. Prod. 77:1670-1677 (2014).

"Intranasal medication delivery—brief overview of the concept." Intranasal.net. Accessed Feb. 24, 2017.

Io Therapeutics, Inc. Brochure for the Symposium on IRX4204 at the 11th International Conference on Alzheimer's and Parkinson's Diseases (2013).

Jassem et al., A randomized phase III trial comparing bexarotene/cisplatin/vinorelbine versus cisplatin/vinorelbine in chemotherapy-naive-patients with advanced or metastatic non-small cell lung cancer (NSCLC). Journal of Clinical Oncology, 2005 ASCO Annual Meeting Proceedings, vol. 23, No. 16S, Part I of II (Jun. 1 Supllement), Abstract 7024.

Johnson et al., Synthesis and biological activity of high-affinity retinoic acid receptor antagonists. Bioorganic & Medicinal Chemistry, vol. 7, No. 7, pp. 1321-1338 (1999).

Kagechika et al., Synthetic retinoids: recent developments concerning structure and clinical utility. Journal of Medicinal Chemistry, vol. 48, No. 19: 5875-5883, (2005).

Kawata et al., RXR partial agonist produced by side chain repositioning of alkoxy RXR full agonist retains antitype 2 diabetes activity without the adverse effects. J. Med. Chem. 58(2):912-926 (2015).

(56) References Cited

OTHER PUBLICATIONS

Kimura et al., IL-6: Regulator of Treg/Th17 balance. Eur. J. Immunol., 40:1830-1835 (2010).

Kim et al., Immunopathogenesis and therapy of cutaneous T cell lymphoma. Science in Medicine, The JCI Textbook of Molecular Medicine. Editors Marks et al., p. 164 (2007).

Klein et al., Cardiovascular involvement in general medial conditions. Thyroid disease and the heart. Circulation, 116:1725-1735 (2007).

Klein et al., Identification and functional separation of retinoic acid receptor neutral antagonists and inverse agonists. The Journal of Biological Chemistry, vol. 271, No. 37, pp. 22692-22696, 1996.

Knol et al., Absence of modulation of CD4+CD25high regulatory T cells in CTCL patients treated with bexarotene. Experimental Dermatology, 19:e95-e102 (2010).

Kotani et al., A naturally occurring rexinoid, honokiol, can serve as a regulator of various retinoid X receptor heterodimers. Biol. Pharm. Bull. 35(1):1-9 (2012).

Laclair et al., Treatment with bexarotene, a compound that increases apolipoprotein-E, provides no cognitive benefit in mutant APP/PSI mice, Molecular Neurodegeneration 8:18 (10pp) (2013).

Lampen et al., Effects of receptor-selective retinoids on CYP26 gene expression and metabolism of all-trans-retinoic acid in intestinal cells. Drug Metabolism & Disposition, vol. 29, No. 3, pp. 742-747 (2001).

Lefebvre et al., Retinoid X receptors: common heterodimerization partners with distinct functions. Trends Endocrinol. Metab. 21:676-683 (2010).

Levasque et al., Nur77 and retinoid X receptors: crucial factors in dopamine-related neuroadaptation. Trends in Neuroscience, vol. 30, No. 1, pp. 22-30 (2007).

Li et al., Distinct Mechanisms of Glucose Lowering by Specific Agonists for Peroxisomal Proliferator Activated Receptor gamma and Retinoic Acid X Receptors, Journal of Biological Chemistry 280(46):38317-38327, 2005.

Liu et al., Combination Therapy of Insulin-Like Growth Factor Binding Protein-3 and Retinoid X Receptor Ligands Synergize on Prostate Cancer Cell Apoptosis In vitro and In vivo. Clin Cancer Res, 11(13):4851-4856 (2005).

Lowenthal et al., The Ethics of Early Evidence—Preparing for a Possible Breakthrough in Alzheimer's Disease. N Engl J Med., 367(6):488-490 (2012).

Macchia et al., RXR receptor agonist suppression of thryoid function: central effects in the absence of thyroid hormone receptor. Am. J. Physiol. Endocrinol. Metab., vol. 283, pp. E326-E331 (2002).

Mangelsdorf et al., Characterization of three RXR genes that mediate the action of 9-cis retinoic acid. Genes and Development 6:329-344 (1992).

Marketwire 2012: IRX4204 as a Potential Disease-Modifying Treatment for Alzheimer's Disease.

Marks et al., Science in Medicine: The JCI textbook of Molecular Medicine, p. 164 (2007).

Martin et al., Induction of the fatty acid transport protein 1 and acyl-CoA synthase genes by dimer-selective rexinoids suggests that the peroxisome proliferator-activated receptor-retinoid X receptor heterodimer is their molecular target. JBC 275(17):12612-12618 (2000).

McFarland et al., Low dose bexarotene treatment rescues dopamine neurons and restores behavioral function in models of Parkinson's disease. ACS Chem. Neurosci. 4:1430-1438 (2013).

Migliore, Intranasal Delivery of GDNF for the Treatment of Parkinson's Disease. Doctoral Thesis, Pharmaceutical Sciences, Northeastern University, Boston, MA (2008).

Miller et al., Initial clinical trial of a selective retinoid X receptor ligand, LGD1069. J Clin Oncol., 15(2):790-795 (1997).

Monahan et al., Neuroinflammation and peripheral immune infiltration in Parkinson's disease: an autoimmune hypothesis. Cell Transplant, 17:363-372 (2008).

Morris & Burns, Insulin: An Emerging Treatment for Alzheimer's Disease Dementia? Curr. Neurol. Neurosci. Rep. 12(5):520-527 (2012).

Munhoz et al., Parkinson's disease and thyroid dysfunction. Parkinsonism & Related Disorders, 10(6):381-383 (2004).

National Multiple Sclerosis Society, Medications, accessed May 12, 2017, pp. 1-5.

Natrajan et al., Retinoid X receptor activation reverses age-related deficiencies in myelin debris phagocytosis and remyelination. Brain A Journal of Neurology, 138:3581-3597 (2015).

Nishimaki-Mogami et al., the RXR agonists PA024 and HX630 have different abilities to activate LXR/RXR and to induce ABCA1 expression in macrophage cell lines. Biochemical Pharmacology, 76: 1006-1013 (2008).

Ohsawa et al., Modification of the lipophilic domain of RXR agonists differentially influences activation of RXR heterodimers. ACS Med Chem Lett., 1:521-525 (2010).

Olson et al., Immunomodulation as a neuroprotective and therapeutic strategy for Parkinson's disease. Curr Opin Pharmacol. 26:87-95 (2016).

Park et al., Salvage chemotherapy of gemcitabine, dexamethasone, and cisplatin (GDP) for patients with relapsed or refractory peripheral T-cell lymphomas: a consortium for improving survival of lymphoma (CISL) trial. Ann. Hematol., vol. 94, No. 11, pp. 1845-1851, see abstract (2015).

Perlmann et al., A novel pathway for vitamin A signaling mediated by RXR heterodimerization with NGFI-B and NURR1. Genes & Develop. 9:769-782 (1995).

Petty et al., Weekly paclitaxel (Taxol®), carboplatin (Paraplatin®), and bexarotene (Tagretin®) for the treatment of patients with advanced non-small cell lung cancer: Efficacy results from a Phase I/II study. Journal of Clinical ONcolocy, 2005 ASCO Annual Meeting Proceedings, vol. 23, No. 16S, Part I of II (Jun. 1 Supplement) Abstract 7243 (2005).

Pierrot et al., Targretin Improves Cognitive and Biological Markers in a Patient with Alzheimer's Disease. Journal of Alzheimers Disease, 49:271-276 (2016).

Price et al., Comment on ApoE-directed Therapeutics Rapidly Clear beta-Amyloid and Reverse Deficits in AD Mouse Models. Science 340:924-d (2013).

Ramaswamy et al., Trophic factors therapy in Parkinson's disease. Prog. Brain Res., 175:201-216 (2009).

Ramlau et al., Randomized phase III trial comparing bexarotene (L1069-49)/cisplatin/vinorelbine with cisplatin/vinorelbine in chemotherapy-naïve patients with advanced or metastic non-small-cell lung cancer: Spirit I. J. Clin. Oncol., 26:1886-1892 (2008).

Reynolds et al., Regulatory T cells attenuate Th17 cell-mediated nigrostriatal dopaminergic neurodegneration in a modelof Parkinson's disease. J. Immunol., vol. 184, pp. 2261-2271 (2010).

Riancho et al., Neuroprotective effect of bexarotene in SOD1G93A mouse model of amyotrophic lateral sclerosis. Frontiers in Cellular Neuroscience 9:Article 250 (2015).

Rigas et al., Emerging role of rexinoids in non-small cell lung cancer: Focus on bexarotene. The Oncologist, 10:22-33 (2005).

Rizvi et al., A phase I study of LGD1069 in adults with advanced cancer. Clin. Cancer Res., 5:1658-1664 (1999).

Sacchetti et al., Requirements for heterodimerization between orphan nuclear receptor Nurr1 and Retinoid X Receptors. The Journal of Biological Chemistry, 277(38):35088-35096 (2002).

Salama et al., Role of L-thyroxin in counteracting rotenone induced neurotoxocity in rats. Environmental Toxicology and Pharmacology, 35:270-277 (2013).

Sherman et al., Central hypothyroidism associated with retinoid X receptor-selective ligands. The New England Journal of Medicine, vol. 340, No. 14, pp. 1075-1079 (1999).

Kabbinavar et al., An open-label phase II clinical trial of the RXR agonist IRX4204 in taxane-resistant, castration-resistant metastatic prostate cancer (CRPC). Journal of Clinical Oncology, vol. 32, No. 15 Suppl, p. 5073 (2014).

Supplementary European Search Report for European Patent Application Serial No. 16861059 dated May 16, 2019.

(56) References Cited

OTHER PUBLICATIONS

Silvestroff et al., Cuprizone-induced demyelination in the rat cerebral cortex and thyroid hormone effects on cortical remyelination. Experimental Neurology, 235, pp. 357-367 (2012).
Smit et al., Bexarotene-induced hypothrodism: bexarotene stimulates the peripheral metabolism of thyroid hormones. J. Clin. Endocrinol. Metab., 92(7):2496-2499 (2007).
Suh et al., Prevention and treatment of experimental breast cancer with the combination of a new selective estrogen receptor modulator, Arzoxifene, and a new rexinoid, LG 100268. Clin Cancer Res, 8:3270-3275 (2002).
Takahashi et al., Novel retinoid X receptor antagonists: specific inhibition of retinoid synergism in RXR-RAR heterodimer actions. Journal of Medicinal Chemistry, vol. 45, No. 16, pp. 3327-3330 (2002).
Teng et al., Identification of highly potent retinoic acid receptor alpha-selective antagonists. Journal of Medicinal Chemistry, vol. 40, pp. 2445-2451 (1997).
Tesseur et al., Comment on ApoE-directed Therapeutics Rapidly Clear beta-Amyloid and Reverse Deficits in AD Mouse Models. Science, 340:924-e (2013).
Tovar-Y-Romo et al., Trophic factors as modulators of motor neuron physiology and survival: implications for ALS therapy. Frontiers in Cellular Neuroscience, 8:Article 61 (2014).
Trillo et al., Ascending monoaminergic systems alterations in Alzheimer's disease. Translating basic science into clinical care. Neuroscience and Biobehavioral Riviews, 37:1363-1379 (2013).
U.S. Appl. No. 16/228,217, filed Dec. 20, 2018.
U.S. Appl. No. 15/769,551, filed Apr. 19, 2018.
U.S. Appl. No. 16/083,799, filed Sep. 10, 2018.
U.S. Appl. No. 16/222,518, filed Dec. 17, 2018.
Uslu et al., Doxazosin: a new cytotoxic agent for prostate cancer? BJU International, vol. 85, pp. 672-675 (2000).
Veeraraghavalu et al, Comment on ApoE-directed Therapeutics Rapidly Clear beta-Amyloid and Reverse Deficits in AD Mouse Models. Science 340:924-f, 2013.
Volakakis et al., Nurr1 and Retinoid X Receptor ligands stimulate Ret signaling in dopamine neurons and can alleviate alpha-synuclein disrupted gene expression. J. Neurosci., 35(42):14370-14385 (2015).
Walkley et al., Retinoic acid receptor anatagonism in vivo expands the numbers of precursor cells during granulopoiesis. Leukemia, vol. 16, No. 9, pp. 1763-1772 (2002).
Wallen-Mackenzie et al., Nurr1-RXR heterodimers mediate RXR ligand-induced signaling in neuronal cells. Genes and Development, 17: 3036-3047 (2003).
Wang et al., Selective brain penetrable Nurr1 transactivator for treating Parkinson's disease. Oncotarget 7 (7):7469-7479 (2016).
Wang, (2013) Slide presentation at the Symposium on IRX4204 at the 11th International Conference on Alzheimer's and Parkinson's Diseases: The Novel RXR agonist IRX4204 as a Potential Disease-Modifying Agent in Alzheimer's Disease.
WebMD, Common Drugs and Medicines to Treat Multiple Sclerosis; Drugs & Medications Search, accessed May 12, 2017; pp. 1-3.
Xiao et al., Retinoic acid increases Foxp3+ regulatory T cells and inhibits development of TH17 cells by enhancing TFG-β-driven Smad3 signaling and inhibiting IL-6 and IL-23 receptor expression. The Journal of Immunology, 181: 2277-2284 (2008).
Xiao et al., Adenomatous polyposis coli (APC)-independent regulation of beta-catenin degradation via a retinoid X receptor-mediated pathway. Journal of Biological Chemistry, vol. 278, No. 32, pp. 29954-29962 (2003).
Yacila & Sari, Potential Therapeutic Drugs and Methods for the Treatment of Amyotrophic Lateral Sclerosis. Curr. Med. Chem., 21(31):3583-3593 (2014).
Yamada et al., Retinoid X receptor ligands: a patent review (2007-2013). Expert Opin. Ther. Patents, 24(4):443-452 (2014).
Zapata-Gonzalez et al., 9-cis-retinoic acid (9cRA), a retinoid X receptor (RXR) ligand, exerts immunosuppressive effects on dendritic cells by RXR-dependent activation: inhibition of peroxisome proliferator-activated receptor gamma blocks some of the 9cRA activities, and precludes them to mature phenotype development. The Journal of Immunogloy, 178:6130-6139 (2007).
Zhang et al., Thyroid hormone potentially benefits multiple sclerosis via facilitating remyelination. Mol. Neurobiol., 53, pp. 4406-4416 (2016).
U.S. Appl. No. 16/296,012, filed Mar. 7, 2019.
Extended European Search Report for EP16893790.2 dated Oct. 1, 2019.
Alcala-Barraza et al., Intranasal delivery of neurotrophic factors BDNF, CNTF, EPO, and NT-4 to the CNS. Journal of Drug Targeting, 18(3):179-190 (2009).
Altucci L et al., RAR and RXR modulation in cancer and metabolic disease. Nature Review Drug Discovery, vol. 6: 793-810 (2007).
Alzforum 2013: Can Cancer Therapy Be Neurodegenerative Wonder Drug?
Annerbo et al., Review Article: A clinical review of the association of thyroid stimulating hormone and cognitive impairment. ISRN Endocrinology, vol. 2013, Article ID 856017, 6 pages (2013).
Balasubramanian et al., Suppression of human pancreatic cancer cell proliferation by AGN194204, an RXR-selective retinoid. Carcinogenesis, 2004, vol. 25, No. 8, pp. 1377-1385.
Balducci et al., The Continuing Failure of Bexarotene in Alzheimer's Disease Mice. J Alzheimers Dis., 46:471-482 (2015).
Benson et al., All-trans retinoic acid mediates enhanced T reg cell growth, differentiation, and gut homing in the face of high levels of co-stimulation. The Journal of Experimental Medicine, vol. 204, No. 8, pp. 1765-1774 (2007).
Beyer et al., Weight change and body composition in patients with Parkinson's disease. J. Am. DietAssoc., vol. 95, pp. 979-983 (1995).
Bilbao et al., Insulin-like growth factor-1 stimulates regulatory T cells and suppresses autoimmune disease. EMBO Mol. Med., 6(11):1423-1435 (2014).
Blumenschein et al., A randomized phase III trial comparing bexarotene/carboplatin/paclitaxel versus carboplatin/paclitaxel in chemotherapy-naive patients with advanced or metastatic non-small cell lung cancer (NSCLC). Journal of Clinical Oncology, 2005 ASCO Annual Meeting Proceedings, vol. 23, No. 16S, Part I of II, Abstract 7001 (2005).
Bordoni et al., Bexarotene improves TTP in untreated, advanced NSCLC, when given in combination with carboplalin/paclitaxel. Journal of Clinical Oncology, ASCO 2005 Annual Meeting, Abstract 7270.
Breen et al., Regulation of Thyroid-Stimulating Hormone beta-Subunit and Growth Hormone Messenger Ribonucleic Acid Levels in the Rat: Effect of Vitamin A Status, Endocrinology 136:543-9 (1995).
Cal et al., Doxazosin: a new cytotoxic agent for prostate cancer? BJU Int. 85:672-675 (2000).
Calza et al., Thyroid hormone activates oligodendrocyte precursors and increases a myelin-forming protein and NGF content in the spinal cord during experimental allergic encephalomyelitis. PNAS, vol. 99, No. 5, pp. 3258-3263 (2002).
Coya et al., Retinoic Acid Inhibits In Vivo Thyroid-Stimulating Hormone Secretion, Life Sciences, Pharmacology Letters, 60:247-50, 1997.
Cramer et al., ApoE-directed therapeutics rapidly clear β-amyloid and reverse deficits in AD mouse models. Science, 335(6075):1503-1506 (2012).
Crowe et al.,A retinoid X receptor (RXR)-selective retinoid reveals that RXR-alpha is potentially a therapeutic target in breast cancer cell lines, and that it potentiates antiproliferative and apoptotic responses to peroxisome proliferator-activated receptor ligands. Breast Cancer Res., vol. 6, No. 5, pp. R546-R555 (2004).
Cummings et al., Double-blind, placebo-controlled, proof-of-concept trial of bexarotene Xin moderate Alzheimer's disease. Alzheimer's Research & Therapy, 8:4 (2016).
Debnath & Berk, Th17 Pathway—Mediated Immunopathogenesis of Schizophrenia: Mechanisms and Implications. Schizophrenia Bulletin, 40(6):1412-1421 (2014).

(56) References Cited

OTHER PUBLICATIONS

Dell'Acqua ML et al., Functional and molecular evidence of myelin- and neuroprotection by thyroid hormone administration in experimental allergic encephalomyelitis. Neuropath. Appl. Neurobiol., 38:454-470 (2012).
D'Intino G et al., Triiodothyronine administration ameliorates the demyelination/remyelination ratio in a non-human primate model of multiple sclerosis by corrected tissue hypothyroidism. J Neuroendocrin., 23:778-790 (2011).
Dore et al., Insulin-like growth factor I protects and rescues hippocampal neurons against beta-amyloid- and human amylin-induced toxicity. Proc. Natl. Acad. Sci. USA, 94:4772-4777 (1997).
Duvic et al., Phase 2 and 3 Clinical Trial of Oral Bexarotene (Targretin Capsules) for the Treatment of Refractory or Persistent Early-Stage Cutaneous T-Cell Lymphoma, Arch Dermatol. 137:581-593, 2001.
Estephan et al., Phase II trial of gemcitabine (G), carboplatin (C) and bexarotene (B) in patients (pts) with newly diagnosed, locally-advanced or metastatic non-small cell carcinoma of the lung. Journal of Clinical Oncology, 2005 ASCO Annual Meeting Proceedings, vol. 23, No. 16S, Part I of II (Jun. 1 Supplement, Abstract 7308 (2005).
Elias et al., Retinoic acid inhibits TH17 polarization and enhances FoxP3 expression through a Stat-3/Stat-5 independent signaling pathway. Blood, vol. 111, No. 3, pp. 1013-1020 (2008).
Fitz et al., Comment on ApoE-directed Therapeutics Rapidly Clear beta-Amyloid and Reverse Deficits in AD Mouse Models. Science 340:924-c (2013).
Franco et al., Thyroid hormones promote differentiation of oligodendrocyte progenitor cells and improve remyelination after cuprizone-induced demyelination. Experimental Neurology, 212, pp. 458-467, 2008 (2008).
Freiherr et al., Intranasal Insulin as a Treatment for Alzheimer's Disease: A Review of Basic Research and Clinical Evidence. CNS Drugs 27:505-514 (2013).
Friling et al., Activation of retinoid X receptor increases dopamine cell survival in models for Parkinson's disease. BMC Neuroscience, 10: 146 (2009).
Fu et al., Thyroid hormone prevents cognitive deficit in a mouse model of Alzheimer's disease. Neuropharmacology, 58:722-729 (2010).
Gibb et al., The substantia nigra and ventral tegmental area in Alzheimer's disease and Down's sydrome. J. Neurol. Neurosurg. and Psychiatry, 52:193-200 (1989).
Golub et al., Molecular classification of cancer: Class discovery and class prediction by gene expression monitoring. Science, vol. 286, Oct. 15, 1999, pp. 531-537.
Gonzalez et al., T-cell-mediated regulation of neuroinflammation involved in neurodegenerative diseases. J Neuroinflam 11:201-212 (2014).
Govindan et al., Phase II trial of bexarotene capsules in patients with non-small-cell lung cancer (NSCLC) who have failed at least 2 prior systemic therapies for Stage 111B/IV disease. Journal of Clinical Oncology, 2005 ASCO Annual Meeting Proceedings, vol. 23, No. 16S, Part I of II, Abstract 7116 (2005).
Graber et al., Protective autoimmunity in the nervous system. Pharmacol. Therapeut., 121:147-159 (2009).
Haugen et al., The Thyrotrope-Restricted Isoform of the Retinoid-X Receptor-y1 Mediates 9-cis-Retinoic Acid Suppression of Thyrotropin-beta Promoter Activity. Molecular Endocrinology 11:481-9, 1997.
Henkel et al., Regulatory T-lymphocytes mediate amyotrophic lateral sclerosis progression and survival. EMBO Mol. Med., 5:64-79 (2012).
Hu et al., Imbalance between IL-17A-Producing Cells and Regulatory T Cells during Ischemic Stroke. Mediators of Inflammation 2014: Article ID 813045, 2014.
Huang et al., Retinoid X receptor gamma signaling accelerates CNS remyelination, Nature Neuroscience, 14(1): 45-53, 2011 (Epub Dec. 5, 2010).
International Search Report and Written Opinion dated Mar. 28, 2013 for International Application Serial No. PCT/US2012/069566 filed on Dec. 13, 2012.
International Search Report and Written Opinion dated Jan. 5, 2017 for International Application Serial No. PCT/US2016/059770 filed Oct. 31, 2016.
International Search Report for PCT/US2007/011730 dated May 2, 2008.
International Search Report and Written Opinion dated Sep. 25, 2007 for International Application No. PCT/US2006/038252 filed on Oct. 2, 2006.
International Search Report and Written Opinion dated Dec. 29, 2016 for International Application No. PCT/US2016/059775 filed on Oct. 31, 2016.
International Search Report and Written Opinion dated Jan. 10, 2017 for International Application No. PCT/US2016/059776 filed on Oct. 31, 2016.
International Search Report and Written Opinion dated Dec. 29, 2016 for International Application No. PCT/US2016/059779 filed on Oct. 31, 2016.
International Search Report and Written Opinion dated May 22, 2017 for International Application No. PCT/US2016/059772 filed on Oct. 31, 2016.
International Search Report and Written Opinion dated Jan. 18, 2019 for International Application No. PCT/US2018/052031 filed on Sep. 20, 2018.
International Search Report and Written Opinion dated Dec. 11, 2018 for International Application No. PCT/US2018/048876 filed on Aug. 30, 2018.
International Application Serial No. PCT/US2018/052031 filed on Sep. 20, 2018.

* cited by examiner

TREATMENT OF MUSCULAR DISORDERS WITH COMBINATIONS OF RXR AGONISTS AND THYROID HORMONES

RELATED APPLICATIONS

This application is a 35 U.S.C. 371 national phase entry of PCT/US2016/059775, filed Oct. 31, 2016, which claims priority to U.S. Provisional Patent Application No. 62/306,472, filed on Mar. 10, 2016. The entire content of each of these applications is herein incorporated by reference.

FIELD

The present disclosure is directed to methods of treating muscular disorders using Retinoid X Receptor (RXR) agonists in combination with thyroid hormones.

BACKGROUND

Compounds which have retinoid-like biological activity are well known in the art and are described in numerous United States patents including, but not limited to, U.S. Pat. Nos. 5,466,861; 5,675,033; and 5,917,082, all of which are herein incorporated by reference. Preclinical studies with rexinoids, which are agonists of RXRs, suggest that selective activation of Retinoid X Receptors (RXR), which modulate functions associated with differentiation, inhibition of cell growth, apoptosis and metastasis, may be useful in treating a variety of diseases associated with RXR.

Attempts to treat muscular disorders have met with limited success. This is due, in part, to the fact that the etiology of muscular disorders is a complex response based in part on a combination of factors, including, without limitation, genetic make-up of individual, immunodysfunction, enzymatic defect, endocrine dysfunction, metabolic abnormality, gender or hormonal status, bacterial or viral infection, metal or chemical toxin exposure, vaccinations or immunizations, stress, trauma, and/or nutritional deficiencies. Therefore, compounds, compositions, and methods that can treat or reduce a symptom associated with a muscular disorder would be highly desirable.

There are two main types of receptors that mediate the effects of derivatives of vitamin A in mammals (and other organisms), the Retinoic Acid Receptors (RARs) and the Retinoid X Receptors (RXRs). Within each type there are three subtypes designated RAR alpha, RAR beta, and RAR gamma for the RAR family and RXR alpha, RXR beta, and RXR gamma for the RXR family. These receptor types are evolutionarily related but are functionally distinct. The ligands that activate the RARs, referred to as retinoids, and the ligands that activate the RXRs, referred to as rexinoids, elicit quite different biological effects. Retinoic acid (RA), the physiological hormone of all three RARs, has been shown to be an important regulator during embryonic development. RA has been shown to enhance skeletal myogenesis in mouse embryonic stem cells (mESC) and in p19 embryonal carcinoma (EC) cells. In these cell types, RA acted to enhance expression of Pax3 and Meox1, both markers of skeletal muscle progenitor cells, by binding with the RARs to the Pax3 and Meox1 regulatory region.

The association of RXR with peroxisome-proliferator-activated receptors (PPARs) has been show to allow cells to respond to fatty acid molecules. PPAR protein isoforms include PPARα, PPARβ/δ, and PPARγ, and RXR can form a heterodimer with each isoform. PPARα regulates the lipid metabolism and is abundantly expressed in liver, heart, muscle, and kidney. PPARγ is expressed predominantly in macrophages and in adipocytes and regulates adipocyte differentiation, lipid homeostasis, and in inflammation. PPARβ/δ regulates energy balance and lipid and glucose metabolism and is a potential drug target for metabolic syndrome.

Although RAR agonists like RA have been used to treat various disorders, including metabolic disorders and cancer, their usefulness in clinical practice has been limited due to unwanted side effects and counter-therapeutic inflammatory effects. Thus, what are needed are compounds and compositions that promote maintenance of muscle function, but not possess any pro-inflammatory activities and other unwanted side effects associated with RAR pan agonists like RA. Such compounds will be of considerable therapeutic value as immunomodulatory agents.

SUMMARY

The activation of retinoic acid receptors (RAR) by non-selective Retinoic X Receptor (RXR) agonists decreases the efficacy of the RXR agonists in muscular disorders. As such, the efficacy of RXR agonists in muscular disorders can be improved by administering the RXR agonist at a dose which activates RXR but which activates RAR minimally or not at all. It is now proposed that a RXR agonist at a dose which specifically activates only RXRs gives optimal anti-muscular disorder activity when combined with administration of a thyroid hormone. Based on this proposal, novel methods of treating a patient with muscular disorders are disclosed herein.

Thus, disclosed herein is a method of treating a muscular disorder, the method comprising administering to an individual in need thereof a therapeutically effective amount of a RXR agonist and one or more thyroid hormones, wherein administration of the RXR agonist and thyroid hormone treats the muscular disorder in the individual more effectively than treatment with the RXR agonist or thyroid hormone alone.

In one embodiment, the RXR agonist has the structure of Formula II

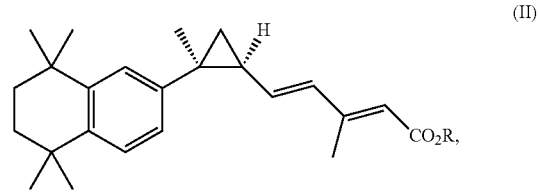

wherein R is H or lower alkyl of 1 to 6 carbons. In some embodiments, the RXR agonist is a selective RXR agonist comprising 3,7-dimethyl-6(S),7(S)-methano,7-[1,1,4,4-tetramethyl-1,2,3,4-tetrahydronaphth-7-yl]2(E),4(E) heptadienoic acid. In other embodiments, the RXR agonist is 3,7-dimethyl-6(S),7(S)-methano,7-[1,1,4,4-tetramethyl-1,2,3,4-tetrahydronaphth-7-yl]2(E),4(E) heptadienoic ethyl ester. In other embodiments, the RXR agonist is bexarotene. In yet other embodiments, the RXR agonist is LG268.

In some embodiments, the thyroid hormone is thyroxine.

In some embodiments, the therapeutically effective amount of the RXR agonist is about 0.001 mg/day to about 1000 mg/day. In certain embodiments, the therapeutically effective amount of the ester of a RXR agonist is about 0.001 mg/day to about 1000 mg/day. In other embodiments, the therapeutically effective amount of the RXR agonist is about 10 mg/day to about 1000 mg/day, or 1 mg/day to 20 mg/day. In yet other embodiments, the therapeutically effective amount of thyroxine is about 12.5 µg/day to about 250 µg/day.

In some embodiments, the RXR agonist is administered by nasal administration. In other embodiments, the RXR agonist and thyroxine are both administered by nasal administration. In other embodiments, the RXR agonist is administered orally. In yet other embodiments, the thyroxine is administered orally. And in still other embodiments, the thyroxine is administered subcutaneously.

In certain embodiments, the RXR agonist and the thyroxine are both administered substantially simultaneously. In other embodiments, the RXR agonist and thyroxine are administered on different schedules.

In some embodiments, the method treats a muscle wasting disorder selected from the group consisting of acid maltase deficiency, atony, atrophy, ataxia, Becker Muscular Dystrophy (BMD), cardiac muscle ischemia, cardiac muscle infarction, a cardiomyopathy, carnitine deficiency, carnitine palmitoyltransferase deficiency, Central Core Disease (CCD), centronuclear (myotubular) myopathy, cerebral palsy, compartment syndromes, channelopathies, Congenital Muscular Dystrophy (CMD), corticosteroid myopathy, cramps, dermatomyositis, distal muscular dystrophy, Duchenne Muscular Dystrophy (DMD), dystrophinopathies, Emery-Dreifuss Muscular Dystrophy (EDMD), Facioscapulohumeral Muscular Dystrophy (FSHD), fibromyalgia, fibrositis, Limb Girdle Muscular Dystrophy (LGMD), McArdle syndrome, muscular dystrophy, muscle fatigue, myasthenia gravis, myofascial pain syndrome, myopathy, myotonia, Myotonic Muscular Dystrophy type 1, Myotonic Muscular Dystrophy type 2, Nemaline myopathy, Oculopharyngeal Muscular Dystrophy (OCM), myoglobinuria, paramyotonia congenita (Eulenberg's disease), polymyositis, rhabdomyolysis, sarcoglycanopathies, or spasms.

In some embodiments, the myopathy is dermatomyositis, inclusion body myositis, or polymyositis.

In certain embodiments, the muscular disorder is due to cancers, HIV/AIDS, COPD, chronic steroid use, fibromyalgia, or skeletal muscle myopathies.

In other embodiments, the combination of rexinoids and thyroid hormones are beneficial by effecting heart muscle protection or regeneration either in vivo, or in vitro for subsequent implantation of myocytes into damaged cardiac muscle.

Also provided herein is a method of treating a muscular disorder, the method comprising of administering to an individual in need thereof a therapeutically effective amount of 3,7-dimethyl-6(S),7(S)-methano,7-[1,1,4,4-tetramethyl-1,2,3,4-tetrahydronaphth-7-yl]2(E),4(E) heptadienoic acid, and thyroxine; and wherein administration of the combination reduces the severity of the muscular disorder in the individual by slowing or stopping progression, or inducing or hastening repair or regeneration of the affected muscle or muscles more effectively than either the RXR agonist or thyroxine alone.

BRIEF DESCRIPTION OF THE DRAWINGS

FIG. 6B: 1 nM IRX4204; FIG. 6C: 0.1 nM IRX4204). * P<0.0001;  P<0.01.

FIG. 9A depicts the myelinated axons per CC unit; FIG. 9B depicts the density of myelinated axons (per 10,000 $\mu m^2$); and FIG. 9C depicts the density of SM132+ ovoids (per 250,000 $\mu m^2$).

DETAILED DESCRIPTION

Figure 1:
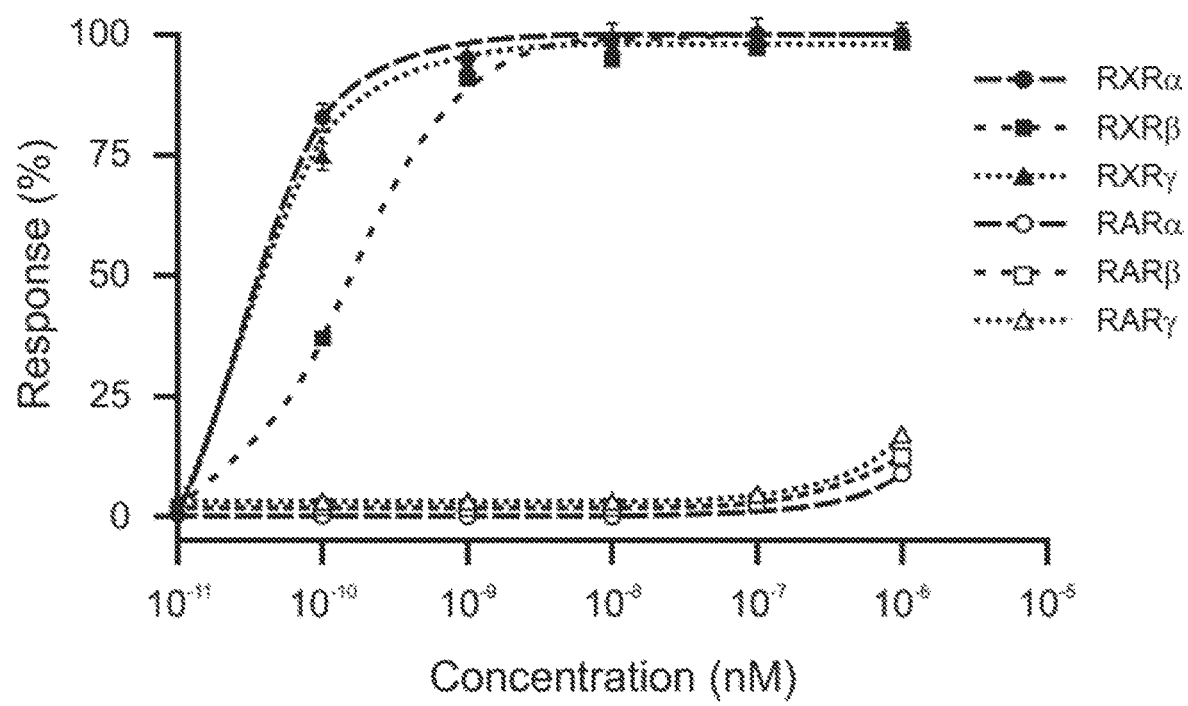
FIG. 1 shows RXR agonist activation of transcription from RXRα, RXRβ, RXRγ, RARα, RARβ, and RARγ using transactivation assays.

Preclinical studies with rexinoids suggest that selective activation of Retinoid X Receptors (RXR), which modulate functions associated with differentiation, inhibition of cell growth, apoptosis and metastasis, may be useful in treating a variety of diseases associated with RXR.

The RARs and RXRs and their cognate ligands function by distinct mechanisms. RAR means one or more of RAR α, β, and γ. RXR generally means one or more of RXR α, β and γ. A RAR biomarker is a distinctive biological, biochemical or biologically derived indicator that signifies patient RAR activity. RAR biomarkers include, but are not limited to, CYP26 levels, CRBPI levels and the like and combinations thereof.

RAR activation threshold means one or more of (1) a CYP26 level which is 25% increased over baseline, and (2) a CRBPI level 25% increased over baseline. The RARs always form heterodimers with RXRs and these RAR/RXR heterodimers bind to specific response elements in the promoter regions of target genes. The binding of RAR agonists to the RAR receptor of the heterodimer results in activation of transcription of target genes leading to retinoid effects. On the other hand, RXR agonists do not activate RAR/RXR heterodimers. RXR heterodimer complexes like RAR/RXR can be referred to as non-permissive RXR heterodimers as activation of transcription due to ligand-binding occurs only at the non-RXR protein (e.g., RAR); activation of transcription does not occur due to ligand binding at the RXR. RXRs also interact with nuclear receptors other than RARs and RXR agonists may elicit some of its biological effects by binding to such RXR/receptor complexes.

These RXR/receptor complexes can be referred to as permissive RXR heterodimers as activation of transcription due to ligand-binding could occur at the RXR, the other receptor, or both receptors. Examples of permissive RXR heterodimers include, without limitation, peroxisome proliferator activated receptor/RXR (PPAR/RXR), farnesyl X receptor/RXR (FXR/RXR), nuclear receptor related-1 protein (Nurr1/RXR) and liver X receptor/RXR (LXR/RXR). Alternately, RXRs may form RXR/RXR homodimers which can be activated by RXR agonists leading to rexinoid effects. Also, RXRs interact with proteins other than nuclear receptors and ligand binding to an RXR within such protein complexes can also lead to rexinoid effects. Due to these differences in mechanisms of action, RXR agonists and RAR agonists elicit distinct biological outcomes and even in the instances where they mediate similar biological effects, they do so by different mechanisms. Moreover, the unwanted side effects of retinoids, such as pro-inflammatory responses or mucocutaneous toxicity, are mediated by activation of one or more of the RAR receptor subtypes. Stated another way, biological effects mediated via RXR pathways would not induce pro-inflammatory responses, and thus, would not result in unwanted side effects.

Thus, aspects of the present specification provide, in part, a RXR agonist. As used herein, the term "RXR agonist", is synonymous with "RXR selective agonist" and refers to a compound that selectively binds to one or more RXR receptors like a RXRα, a RXRβ, or a RXRγ in a manner that elicits gene transcription via an RXR response element. As used herein, the term "selectively binds," when made in reference to a RXR agonist, refers to the discriminatory binding of a RXR agonist to the indicated target receptor like a RXRα, a RXRβ, or a RXRγ such that the RXR agonist does not substantially bind with non-target receptors like a RARα, a RARβ, or a RARγ. In some embodiments, the term "RXR agonist" includes esters of RXR agonists.

In one embodiment, the selective RXR agonist does not activate to any appreciable degree the permissive heterodimers PPAR/RXR, FXR/RXR, and LXR/RXR. In another embodiment, the RXR agonist, activates the permissive heterodimer Nurr1/RXR. One example of such a selective RXR agonist is 3,7-dimethyl-6(S),7(S)-methano,7-[1,1,4,4-tetramethyl-1,2,3,4-tetrahydronaphth-7-yl]2(E),4(E) heptadienoic acid (IRX4204) disclosed herein, the structure of which is shown in Formula III. In other aspects of this embodiment, the RXR agonists, activates the permissive heterodimers PPAR/RXR, FXR/RXR, or LXR/RXR by 1% or less, 2% or less, 3% or less, 4% or less, 5% or less, 6% or less, 7% or less, 8% or less, 9% or less, or 10% or less relative to the ability of activating agonists to the non-RXR receptor to activate the same permissive heterodimer. Examples of RXR agonists, which activates one or more of PPAR/RXR, FXR/RXR, or LXR/RXR include, LGD1069 (bexarotene) and LGD268.

IRX4204, like some other RXR ligands, does not activate non-permissive heterodimers such as RAR/RXR. However, IRX4204, is unique in that it specifically activates the Nurr1/RXR heterodimer and does not activate other permissive RXR heterodimers such as PPAR/RXR, FXR/RXR, and LXR/RXR. Other RXR ligands generally activate these permissive RXR heterodimers. Thus, all RXR ligands cannot be classified as belonging to one class. IRX4204 belongs to a unique class of RXR ligands which selectively activate RXR homodimers and only one of the permissive RXR heterodimers, namely the Nurr1/RXR heterodimer.

Binding specificity is the ability of a RXR agonist, to discriminate between a RXR receptor and a receptor that does not contain its binding site, such as a RAR receptor.

More specifically, disclosed herein are esters of RXR agonists. An ester may be derived from a carboxylic acid of C1, or an ester may be derived from a carboxylic acid functional group on another part of the molecule, such as on a phenyl ring. While not intending to be limiting, an ester may be an alkyl ester, an aryl ester, or a heteroaryl ester. The term alkyl has the meaning generally understood by those skilled in the art and refers to linear, branched, or cyclic alkyl moieties. $C_{1-6}$ alkyl esters are particularly useful, where alkyl part of the ester has from 1 to 6 carbon atoms and includes, but is not limited to, methyl, ethyl, propyl, isopropyl, n-butyl, sec-butyl, iso-butyl, t-butyl, pentyl isomers, hexyl isomers, cyclopropyl, cyclobutyl, cyclopentyl, cyclohexyl, and combinations thereof having from 1-6 carbon atoms, etc.

Thus, disclosed herein are RXR agonists, or esters thereof, having the structure of formula I:

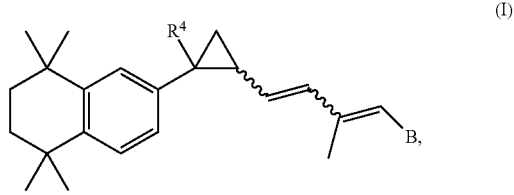

(I)

where $R^4$ is lower alkyl of 1 to 6 carbons; B is —$COOR^8$ where $R^8$ is lower alkyl of 1 to 6 carbons, and the configuration about the cyclopropane ring is cis, and the configuration about the double bonds in the pentadienoic acid or ester chain attached to the cyclopropane ring is trans in each of the double bonds.

In an exemplary embodiment, an ester of a RXR agonist is a compound having the structure of formula II:

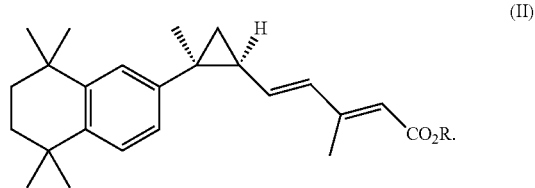

(II)

wherein R is lower alkyl of 1 to 6 carbons.

In a further exemplary embodiment, a RXR agonist may be a selective RXR agonist comprising 3,7-dimethyl-6(S), 7(S)-methano,7-[1,1,4,4-tetramethyl-1,2,3,4-tetrahydronaphth-7-yl]2(E),4(E) heptadienoic acid (IRX4204) or esters thereof, and has the structure of formula III:

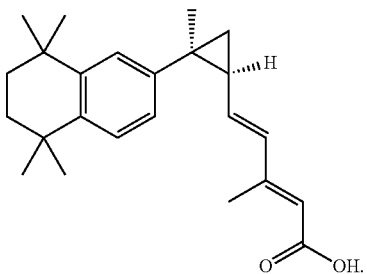

(III)

In certain embodiments, the RXR agonist may be bexarotene (TARGRETIN®, 4-[1-(3,5,5,8,8-pentamethyl-6,7-dihydronaphthalen-2-yl)ethenyl]benzoic acid, LGD1069, Mylan Pharmaceuticals, Inc.), or esters thereof, and has the structure of formula IV:

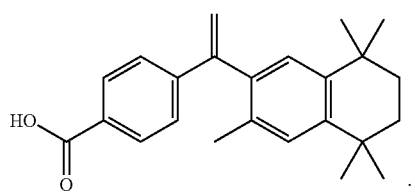

(IV)

In other embodiments, the RXR agonist may be LG268 (LG100268, LGD268, 2-[1-(3,5,5,8,8-pentamethyl-5,6,7,8-tetrahydro-2-naphthyl)cyclopropyl]pyridine-5-carboxylic acid), or esters thereof and has the structure of formula V:

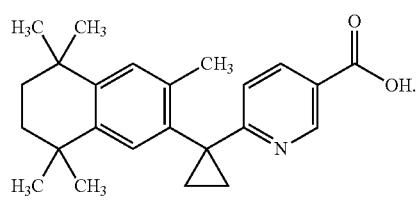

(V)

Pharmaceutically acceptable salts of RXR agonists, or esters thereof, can also be used in the disclosed method. Compounds disclosed herein which possess a sufficiently acidic, a sufficiently basic, or both functional groups, and accordingly can react with any of a number of organic or inorganic bases, and inorganic and organic acids, to form a salt.

Administration of RXR agonists, or esters thereof, may lead to the suppression of serum thyroid hormones and possibly to hypothyroidism and related conditions. In some embodiments, a thyroid hormone may be used in combination with the RXR agonists, or esters thereof. As used herein, the term "thyroid hormone" refers to thyroxine and triiodothyronine. Thyroxine (thyroid hormone $T_4$, levothyroxine sodium) is a tyrosine-based hormone produced by the thyroid gland and is primarily responsible for regulation of metabolism. Thyroxine is a prohormone for triiodothyronine ($T_3$). RXR agonists are known to suppress thyroid function. However, supplementation of RXR agonist therapy with thyroid hormones has not been utilized therapeutically to enhance the effects of the RXR agonist.

Aspects of the present specification provide, in part, a composition comprising a RXR agonists, or esters or other derivatives thereof, and compositions comprising a RXR agonist, or esters or other derivatives thereof, and a thyroid hormone. Exemplary RXR agonists are IRX4204, bexarotene, and LG268. Exemplary esters of RXR agonists are IRX4204 ethyl ester (IRX4204EE), an ester of bexarotene, and an ester of LG268.

Aspects of the methods of the present disclosure include, in part, treatment of a mammal. A mammal includes a human, and a human can be a patient. Other aspects of the present disclosure provide, in part, an individual. An individual includes a mammal and a human, and a human can be a patient.

RXR agonists, or esters thereof, disclosed herein, or a composition comprising an RXR agonists or esters thereof, or a combination of RXR agonists, or esters thereof, and a thyroid hormone, such as thyroxine, is generally administered to an individual as a pharmaceutical composition.

Pharmaceutical compositions may be prepared by combining a therapeutically effective amount of at least one RXR agonist, as an active ingredient, with conventional acceptable pharmaceutical excipients, and by preparation of unit dosage forms suitable for therapeutic use. As used herein, the term "pharmaceutical composition" refers to a therapeutically effective concentration of an active compound, such as any of the compounds disclosed herein. Preferably, the pharmaceutical composition does not produce an adverse, allergic, or other untoward or unwanted reaction when administered to an individual. A pharmaceutical composition disclosed herein is useful for medical and veterinary applications. A pharmaceutical composition may be administered to an individual alone, or in combination with other supplementary active compounds, agents, drugs or hormones. The pharmaceutical compositions may be manufactured using any of a variety of processes, including, without limitation, conventional mixing, dissolving, granulating, dragee-making, levigating, emulsifying, encapsulating, entrapping, and lyophilizing. The pharmaceutical composition can take any of a variety of forms including, without limitation, a sterile solution, suspension, emulsion, lyophilizate, tablet, pill, pellet, capsule, powder, syrup, elixir, or any other dosage form suitable for administration.

A pharmaceutical composition produced using the methods disclosed herein may be a liquid formulation, semi-solid formulation, or a solid formulation. A formulation disclosed herein can be produced in a manner to form one phase, such as, but not limited to an oil or a solid. Alternatively, a formulation disclosed herein can be produced in a manner to form two phases, such as an emulsion. A pharmaceutical composition disclosed herein intended for such administration may be prepared according to any method known to the art for the manufacture of pharmaceutical compositions.

Liquid formulations suitable for parenteral injection or for nasal sprays may comprise physiologically acceptable sterile aqueous or nonaqueous solutions, dispersions, suspensions or emulsions and sterile powders for reconstitution into sterile injectable solutions or dispersions. Formulations suitable for nasal administration may comprise physiologically acceptable sterile aqueous or nonaqueous solutions, dispersions, suspensions or emulsions. Examples of suitable aqueous and nonaqueous carriers, diluents, solvents or vehicles include, but are not limited to, water, ethanol, polyols (propylene glycol, polyethyleneglycol (PEG), glycerol, and the like), suitable mixtures thereof, vegetable oils (such as olive oil or peanut oil) and injectable organic esters such as ethyl oleate. Proper fluidity can be maintained, for example, by the use of a coating such as lecithin, by the maintenance of the required particle size in the case of dispersions and by the use of surfactants.

Aqueous suspensions may include pharmaceutically acceptable excipients such as, but not limited to, a) suspending agents, as for example, sodium carboxymethyl cellulose, methylcellulose, hydroxypropylmethylcellulose, sodium alginate, polyvinylpyrrolidone, gum tragacanth and gum acacia; b) dispersing or wetting agents, as for naturally occurring phosphatide or lecithin, or condensation products of an alkylene oxide with fatty acids, such as, but not limited to, polyoxyethylene stearate, or condensation products of ethylene oxide with long chain aliphatic alcohols, such as, but not limited to, heptadecaethylene-oxycetanol, or condensation products of ethylene oxide with partial esters derived from fatty acids and a hexitol, such as polyoxyethylene sorbitol monoleate or condensation products of ethylene oxide with partial esters derived from fatty acids and hexitol anhydrides, such as, but not limited to, polyoxyethylene sorbitan monoleate. The aqueous suspensions can also contain one or more preservatives, ethyl- or -n-propyl-p-hydroxy benzoate, one or more coloring agents, one or more flavoring agents and one or more sweetening agents, such as, but not limited to, sucrose, saccharin or sodium or calcium cyclamate.

Pharmaceutical formulations suitable for administration by inhalation include fine particle dusts or mists, which may be generated by means of various types of metered, dose pressurized aerosols, nebulizers, or insufflators.

Semi-solid formulations suitable for topical administration include, without limitation, ointments, creams, salves, and gels. In such solid formulations, the active compound may be admixed with at least one inert customary excipient (or carrier) such as, but not limited to, a lipid and/or polyethylene glycol.

Solid formulations suitable for oral administration include capsules, tablets, pills, powders and granules. In such solid formulations, the active compound may be admixed with at least one inert customary excipient (or carrier) such as, but not limited to, sodium citrate or dicalcium phosphate or (a) fillers or extenders, for example but not limited to, starches, lactose, sucrose, glucose, mannitol and silicic acid, (b) binders, for example but not limited to, carboxymethylcellulose, alignates, gelatin, polyvinylpyrrolidone, sucrose and acacia, (c) humectants, for example, but not limited to, glycerol, (d) disintegrating agents, for example, but not limited to, agar-agar, calcium carbonate, potato or tapioca starch, alginic acid, certain complex silicates and sodium carbonate, (e) solution retarders, for example, but not limited to, paraffin, (f) absorption accelerators, for example, but not limited to, quaternary ammonium compounds, (g) wetting agents, for example, but not limited to, cetyl alcohol and glycerol monostearate, (h) adsorbents, for example, but not limited to, kaolin and bentonite, and (i) lubricants, for example, but not limited to, talc, calcium stearate, magnesium stearate, solid polyethylene glycols, sodium lauryl sulfate or mixtures thereof. In the case of capsules, tablets and pills, the dosage forms may also comprise buffering agents.

In liquid and semi-solid formulations, a concentration of an RXR agonist typically may be between about 50 mg/mL to about 1,000 mg/ml. In aspects of this embodiment, a therapeutically effective amount of a therapeutic compound disclosed herein may be from about 50 mg/mL to about 100 mg/mL, about 50 mg/mL to about 200 mg/mL, about 50 mg/mL to about 300 mg/mL, about 50 mg/mL to about 400 mg/mL, about 50 mg/mL to about 500 mg/mL, about 50 mg/mL to about 600 mg/mL, about 50 mg/mL to about 700 mg/mL, about 50 mg/mL to about 800 mg/mL, about 50 mg/mL to about 900 mg/mL, about 50 mg/mL to about 1,000 mg/mL, about 100 mg/mL to about 200 mg/mL, about 100 mg/mL to about 300 mg/mL, about 100 mg/mL to about 400 mg/mL, about 100 mg/mL to about 500 mg/mL, about 100 mg/mL to about 600 mg/mL, about 100 mg/mL to about 700 mg/mL, about 100 mg/mL to about 800 mg/mL, about 100 mg/mL to about 900 mg/mL, about 100 mg/mL to about 1,000 mg/mL, about 200 mg/mL to about 300 mg/mL, about 200 mg/mL to about 400 mg/mL, about 200 mg/mL to about 500 mg/mL, about 200 mg/mL to about 600 mg/mL, about 200 mg/mL to about 700 mg/mL, about 200 mg/mL to about 800 mg/mL, about 200 mg/mL to about 900 mg/mL, about 200 mg/mL to about 1,000 mg/mL, about 300 mg/mL to about 400 mg/mL, about 300 mg/mL to about 500 mg/mL, about 300 mg/mL to about 600 mg/mL, about 300 mg/mL to about 700 mg/mL, about 300 mg/mL to about 800 mg/mL, about 300 mg/mL to about 900 mg/mL, about 300 mg/mL to about 1,000 mg/mL, about 400 mg/mL to about 500 mg/mL, about 400 mg/mL to about 600 mg/mL, about 400 mg/mL to about 700 mg/mL, about 400 mg/mL to about 800 mg/mL, about 400 mg/mL to about 900 mg/mL, about 400 mg/mL to about 1,000 mg/mL, about 500 mg/mL to about 600 mg/mL, about 500 mg/mL to about 700 mg/mL, about 500 mg/mL to about 800 mg/mL, about 500 mg/mL to about 900 mg/mL, about 500 mg/mL to about 1,000 mg/mL, about 600 mg/mL to about 700 mg/mL, about 600 mg/mL to about 800 mg/mL, about 600 mg/mL to about 900 mg/mL, about 600 mg/mL to about 1,000 mg/mL, or any other range bound by these values.

In semi-solid and solid formulations, an amount of a RXR agonist may be between about 0.01% to about 45% by weight. In aspects of this embodiment, an amount of a therapeutic compound disclosed herein may be from about 0.1% to about 45% by weight, about 0.1% to about 40% by weight, about 0.1% to about 35% by weight, about 0.1% to about 30% by weight, about 0.1% to about 25% by weight, about 0.1% to about 20% by weight, about 0.1% to about 15% by weight, about 0.1% to about 10% by weight, about 0.1% to about 5% by weight, about 1% to about 45% by weight, about 1% to about 40% by weight, about 1% to about 35% by weight, about 1% to about 30% by weight, about 1% to about 25% by weight, about 1% to about 20% by weight, about 1% to about 15% by weight, about 1% to about 10% by weight, about 1% to about 5% by weight, about 5% to about 45% by weight, about 5% to about 40% by weight, about 5% to about 35% by weight, about 5% to about 30% by weight, about 5% to about 25% by weight, about 5% to about 20% by weight, about 5% to about 15% by weight, about 5% to about 10% by weight, about 10% to about 45% by weight, about 10% to about 40% by weight, about 10% to about 35% by weight, about 10% to about 30% by weight, about 10% to about 25% by weight, about 10% to about 20% by weight, about 10% to about 15% by weight, about 15% to about 45% by weight, about 15% to about 40% by weight, about 15% to about 35% by weight, about 15% to about 30% by weight, about 15% to about 25% by weight, about 15% to about 20% by weight, about 20% to about 45% by weight, about 20% to about 40% by weight, about 20% to about 35% by weight, about 20% to about 30% by weight, about 20% to about 25% by weight, about 25% to about 45% by weight, about 25% to about 40% by weight, about 25% to about 35% by weight, about 25% to about 30% by weight, or any other range bound by these values.

A pharmaceutical composition disclosed herein may optionally include a pharmaceutically acceptable carrier that facilitates processing of an active compound into pharmaceutically acceptable compositions. As used herein, the term "pharmaceutically acceptable" refers to those compounds, materials, compositions, and/or dosage forms which are, within the scope of sound medical judgment, suitable for contact with the tissues of human beings and animals without excessive toxicity, irritation, allergic response, or other problem complications commensurate with a reasonable benefit/risk ratio. As used herein, the term "pharmacologically acceptable carrier" is synonymous with "pharmacological carrier" and refers to any carrier that has substantially no long term or permanent detrimental effect when administered and encompasses terms such as "pharmacologically acceptable vehicle, stabilizer, diluent, additive, auxiliary, or excipient." Such a carrier generally is mixed with an active compound or permitted to dilute or enclose the active compound and can be a solid, semi-solid, or liquid agent. It is understood that the active compounds can be soluble or can be delivered as a suspension in the desired carrier or diluent.

Any of a variety of pharmaceutically acceptable carriers may be used including, without limitation, aqueous media such as water, saline, glycine, hyaluronic acid and the like; solid carriers such as starch, magnesium stearate, mannitol, sodium saccharin, talcum, cellulose, glucose, sucrose, lactose, trehalose, magnesium carbonate, and the like; solvents; dispersion media; coatings; antibacterial and antifungal agents; isotonic and absorption delaying agents; or any other inactive ingredient. Selection of a pharmacologically acceptable carrier can depend on the mode of administration. Except insofar as any pharmacologically acceptable carrier is incompatible with the active compound, its use in pharmaceutically acceptable compositions is contemplated. Non-limiting examples of specific uses of such pharmaceutical carriers can be found in Pharmaceutical Dosage Forms and Drug Delivery Systems (Howard C. Ansel et al., eds., Lippincott Williams & Wilkins Publishers, 7$^{th}$ ed. 1999); Remington: The Science and Practice of Pharmacy (Alfonso R. Gennaro ed., Lippincott, Williams & Wilkins, 20$^{th}$ ed. 2000); Goodman & Gilman's The Pharmacological Basis of Therapeutics (Joel G. Hardman et al., eds., McGraw-Hill Professional, 10$^{th}$ ed. 2001); and Handbook of Pharmaceutical Excipients (Raymond C. Rowe et al., APhA Publications, 4$^{th}$ edition 2003). These protocols are routine and any modifications are well within the scope of one skilled in the art and from the teaching herein.

A pharmaceutical composition disclosed herein may optionally include, without limitation, other pharmaceutically acceptable components (or pharmaceutical components), including, without limitation, buffers, preservatives, tonicity adjusters, salts, antioxidants, osmolality adjusting agents, physiological substances, pharmacological substances, bulking agents, emulsifying agents, wetting agents, sweetening or flavoring agents, and the like. Various buffers and means for adjusting pH may be used to prepare a pharmaceutical composition disclosed herein, provided that the resulting preparation is pharmaceutically acceptable. Such buffers include, without limitation, acetate buffers, borate buffers, citrate buffers, phosphate buffers, neutral buffered saline, and phosphate buffered saline. It is understood that acids or bases can be used to adjust the pH of a composition as needed.

Pharmaceutically acceptable antioxidants include, without limitation, sodium metabisulfite, sodium thiosulfate, acetylcysteine, butylated hydroxyanisole, and butylated hydroxytoluene. Useful preservatives may include, but not limited to, benzalkonium chloride, chlorobutanol, thimerosal, phenylmercuric acetate, phenylmercuric nitrate, a stabilized oxy chloro composition, sodium chlorite and chelants, DTPA or DTPA-bisamide, calcium DTPA, and CaNaDTPA-bisamide. Tonicity adjustors useful in a pharmaceutical composition may include, but are not limited to, salts such as sodium chloride, potassium chloride, mannitol or glycerin and other pharmaceutically acceptable tonicity adjustor. The pharmaceutical composition may be provided as a salt and can be formed with many acids, including, but not limited to, hydrochloric, sulfuric, acetic, lactic, tartaric, malic, succinic, etc. Salts tend to be more soluble in aqueous or other protonic solvents than are the corresponding free base forms. It is understood that these and other substances known in the art of pharmacology can be included in a pharmaceutical composition useful herein.

The compounds disclosed herein, such as a combination of an RXR agonist and a thyroid hormone, may also be incorporated into a drug delivery platform in order to achieve a controlled compound release profile over time. Such a drug delivery platform may comprise the combination disclosed herein dispersed within a polymer matrix, typically a biodegradable, bioerodible, and/or bioresorbable polymer matrix. As used herein, the term "polymer" refers to synthetic homo- or copolymers, naturally occurring homo- or copolymers, as well as synthetic modifications or derivatives thereof having a linear, branched or star structure. Copolymers can be arranged in any form, such as random, block, segmented, tapered blocks, graft, or triblock. Polymers are generally condensation polymers. Polymers can be further modified to enhance their mechanical or degradation properties by introducing cross-linking agents or changing the hydrophobicity of the side residues. If crosslinked, polymers are usually less than 5% crosslinked, usually less than 1% crosslinked.

Suitable polymers may include, but are not limited to, alginates, aliphatic polyesters, polyalkylene oxalates, polyamides, polyamidoesters, polyanhydrides, polycarbonates, polyesters, polyethylene glycol, polyhydroxyaliphatic carboxylic acids, polyorthoesters, polyoxaesters, polypeptides, polyphosphazenes, polysaccharides, and polyurethanes. The polymer usually comprises at least about 10% (w/w), at least about 20% (w/w), at least about 30% (w/w), at least about 40% (w/w), at least about 50% (w/w), at least about 60% (w/w), at least about 70% (w/w), at least about 80% (w/w), or at least about 90% (w/w) of the drug delivery platform. Examples of biodegradable, bioerodible, and/or bioresorbable polymers and methods useful to make a drug delivery platform are described in U.S. Pat. Nos. 4,756,911; 5,378,475; 7,048,946; and U.S. Patent Publication Nos. 2005/0181017; 2005/0244464; 2011/0008437; each of which is incorporated by reference for all it discloses regarding drug delivery.

In aspects of this embodiment, a polymer composing the matrix may be a polypeptide such as, but not limited to, silk fibroin, keratin, or collagen. In other aspects of this embodiment, a polymer composing the matrix may be a polysaccharide such as, but not limited to, cellulose, agarose, elastin, chitosan, chitin, or a glycosaminoglycan like chondroitin sulfate, dermatan sulfate, keratan sulfate, or hyaluronic acid. In yet other aspects of this embodiment, a polymer composing the matrix may be a polyester such as D-lactic acid, L-lactic acid, racemic lactic acid, glycolic acid, caprolactone, and combinations thereof.

One of ordinary skill in the art appreciates that the selection of a suitable polymer for forming a suitable disclosed drug delivery platform depends on several factors. The more relevant factors in the selection of the appropriate polymer(s), include, without limitation, compatibility of polymer with drug, desired release kinetics of drug, desired biodegradation kinetics of platform at implantation site, desired bioerodible kinetics of platform at implantation site, desired bioresorbable kinetics of platform at implantation site, in vivo mechanical performance of platform, processing temperatures, biocompatibility of platform, and patient tolerance. Other relevant factors that, to some extent, dictate the in vitro and in vivo behavior of the polymer include the chemical composition, spatial distribution of the constituents, the molecular weight of the polymer and the degree of crystallinity.

A drug delivery platform may include both a sustained release drug delivery platform and an extended release drug delivery platform. As used herein, the term "sustained release" refers to the release of a compound disclosed herein over a period of about seven days or more. As used herein, the term "extended release" refers to the release of a compound disclosed herein over a period of time of less than about seven days.

In aspects of this embodiment, a sustained release drug delivery platform may release a RXR agonist disclosed herein, or the combination an RXR agonist and a thyroid hormone, with substantially first order release kinetics over a period of about 7 days after administration, about 15 days after administration, about 30 days after administration, about 45 days after administration, about 60 days after administration, about 75 days after administration, or about 90 days after administration. In other aspects of this embodiment, a sustained release drug delivery platform releases a compound disclosed herein with substantially first order release kinetics over a period of at least 7 days after administration, at least 15 days after administration, at least 30 days after administration, at least 45 days after administration, at least 60 days after administration, at least 75 days after administration, or at least 90 days after administration.

In aspects of this embodiment, a drug delivery platform may release a RXR agonist disclosed herein, or the combination of an RXR agonist and a thyroid hormone, with substantially first order release kinetics over a period of about 1 day after administration, about 2 days after administration, about 3 days after administration, about 4 days after administration, about 5 days after administration, or about 6 days after administration. In other aspects of this embodiment, a drug delivery platform releases a compound disclosed herein with substantially first order release kinetics over a period of at most 1 day after administration, at most 2 days after administration, at most 3 days after administration, at most 4 days after administration, at most 5 days after administration, or at most 6 days after administration.

Aspects of the present disclosure include, in part, administering a RXR agonist, or a RXR agonist in combination with a thyroid hormone, such as thyroxine. As used herein, the term "administering" means any delivery mechanism that provides a compound, a composition, or a combination disclosed herein to an individual that potentially results in a clinically, therapeutically, or experimentally beneficial result.

Administration of a RXR agonist, in combination with a thyroid hormone, disclosed herein may include individually a variety of enteral or parenteral approaches including, without limitation, oral administration in any acceptable form, such as tablet, liquid, capsule, powder, or the like; topical administration in any acceptable form, such as drops, spray, creams, gels or ointments; buccal, nasal, and/or inhalation administration in any acceptable form; rectal administration in any acceptable form; vaginal administration in any acceptable form; intravascular administration in any acceptable form, such as intravenous bolus injection, intravenous infusion, intra-arterial bolus injection, intra-arterial infusion and catheter instillation into the vasculature; pen- and intra-tissue administration in any acceptable form, such as intraperitoneal injection, intramuscular injection, subcutaneous injection, subcutaneous infusion, intraocular injection, retinal injection, or sub-retinal injection or epidural injection; intravesicular administration in any acceptable form, such as catheter instillation; and by placement device, such as an implant, a stent, a patch, a pellet, a catheter, an osmotic pump, a suppository, a bioerodible delivery system, a non-bioerodible delivery system or another implanted extended or slow release system. An exemplary list of biodegradable polymers and methods of use are described in, e.g., *Handbook of Biodegradable Polymers* (Abraham J. Domb et al., eds., Overseas Publishers Association, 1997).

A compound, a composition, or a combination disclosed herein may be administered to a mammal using a variety of routes. Routes of administration suitable for treating a muscular disorder as disclosed herein include both local and systemic administration. Local administration results in significantly more delivery of a compound, a composition, or a combination to a specific location as compared to the entire body of the mammal, whereas, systemic administration results in delivery of a compound, a composition, or a combination to essentially the entire body of the individual.

The actual route of administration of a compound, a composition, or a combination disclosed herein used can be determined by a person of ordinary skill in the art by taking into account factors, including, without limitation, the duration of treatment desired, the degree of relief desired, the duration of relief desired, the particular compound, composition, or combination, the rate of excretion of the compound, composition, or combination used, the pharmacodynamics of the compound, composition, or combination used, the nature of the other compounds to be included in the composition or combination, the particular route of administration, the particular characteristics, history and risk factors of the individual, such as, age, weight, general health and the like, the response of the individual to the treatment, or any combination thereof. An effective dosage amount of a compound, a composition, or a combination disclosed herein can thus readily be determined by the person of ordinary skill in the art considering all criteria and utilizing his best judgment on the individual's behalf.

In an embodiment, a compound, a composition, or a combination disclosed herein is administered systemically to a mammal. In another embodiment, a compound, a composition, or a combination disclosed herein is administered locally to a mammal. In an aspect of this embodiment, a compound, a composition, or a combination disclosed herein is administered to the site of a muscular disorder in the mammal.

In other embodiments, RXR agonists may be administered orally, buccally, by nasal, and/or inhalation administration, intravascularly, intravenously, by intraperitoneal injection, intramuscularly, subcutaneously, intraocularly injection, by epidural injection, or by intravesicular administration; and thyroxine may be administered orally or subcutaneously or by another route. The RXR agonists, and the thyroid hormone do not need to be administered by the same route or on the same administration schedule.

Aspects of the present specification provide, in part, administering a therapeutically effective amount of a RXR agonist in combination with a thyroid hormone. As used herein, the term "therapeutically effective amount" is synonymous with "therapeutically effective dose" and when used in reference to treating a muscular disorder means a dose of a compound, a composition, or a combination necessary to achieve the desired therapeutic effect and includes a dose sufficient to reduce tumor burden or place a patient into a clinical remission.

Additionally, where repeated administration of a compound, a composition, or a combination disclosed herein is used, the actual effect amount of compound, composition, or combination disclosed herein will further depend upon factors, including, without limitation, the frequency of administration, the half-life of the compound, composition, or combination disclosed herein. It is known by a person of ordinary skill in the art that an effective amount of a compound or a composition disclosed herein can be extrapolated from in vitro assays and in vivo administration studies using animal models prior to administration to humans. Wide variations in the necessary effective amount are to be expected in view of the differing efficiencies of the various routes of administration. For instance, oral administration generally would be expected to require higher dosage levels than administration by intravenous or intravitreal injection. Variations in these dosage levels can be adjusted using standard empirical routines of optimization, which are well-known to a person of ordinary skill in the art. The precise therapeutically effective dosage levels and patterns are preferably determined by the attending physician in consideration of the above-identified factors.

As a non-limiting example, when administering a RXR agonists disclosed herein to a mammal, a therapeutically effective amount generally may be in the range of about 0.001 mg/day to about 3000 mg/day. In aspects of this embodiment, an effective amount of a compound or a composition disclosed herein may be about 0.01 mg/day to about 0.1 mg/day, about 0.03 mg/day to about 3.0 mg/day, about 0.1 mg/day to about 3.0 mg/day, about 0.3 mg/day to about 3.0 mg/day, about 1 mg/day to about 3 mg/day, about 3 mg/day to about 30 mg/day, about 10 mg/day to about 30 mg/day, about 10 mg/day to about 100 mg/day, about 30 mg/day to about 100 mg/day, about 100 mg/day to about 1000 mg/day, about 100 mg/day to about 300 mg/day, about 1000 mg/day to about 3000 mg/day, about 1 mg/day to about 100 mg/day, or about 1 mg/day to about 20 mg/day. In yet other aspects of this embodiment, a therapeutically effective amount of a compound or a composition disclosed herein may be at least 0.001 mg/kg/day, at least 0.01 mg/day, at least 0.1 mg/day, at least 1.0 mg/day, at least 3.0 mg/day, at least 10 mg/day, at least 30 mg/day, at least 100 mg/day, at least 300 mg/day, or at least 1000 mg/day. In yet other aspects of this embodiment, a therapeutically effective amount of a compound or a composition disclosed herein may be at most 0.001 mg/day, at most 0.01 mg/day, at most 0.1 mg/day, at most 1.0 mg/day, at most 3.0 mg/day, at most 10 mg/day, at most 30 mg/day, at most 100 mg/day, at most 300 mg/day, at most 1000 mg/day, or at most 3000 mg/day.

Suitable thyroxine doses are generally from about 12.5 μg/day to about 250 μg/day orally initially with an increase in dose of about 12.5 to about 25 μg daily increments every 2-4 weeks as needed. In other embodiments, the suitable thyroxine dose is from about 5 μg/day to about 225 μg/day, from about 7.5 μg/day to about 200 μg/day, from about 10 μg/day to about 175 μg/day, from about 12.5 μg/day to about 150 μg/day, from about 15 μg/day to about 125 μg/day, from about 17.5 μg/day to about 100 μg/day, from about 20 μg/day to about 100 μg/day, from about 22.5 μg/day to about 100 μg/day, from about 25 μg/day to about 100 μg/day, from about 5 μg/day to about 200 μg/day, from about 5 μg/day to about 100 μg/day, from about 7.5 μg/day to about 90 μg/day, from about 10 μg/day to about 80 μg/day, from about 12.5 μg/day to about 60 μg/day, or from about 15 μg/day to about 50 μg/day. Increases in dose are generally made in increments of about 5 μg/day, about 7.5 μg/day, about 10 μg/day, about 12.5 μg/day, about 15 μg/day, about 20 μg/day, or about 25 μg/day. In certain embodiments, the suitable thyroid hormone dose is a dose able to produce serum levels of T4 in the top 50%, the top 60%, the top 70%, the top 80%, or the top 90% of the normal range for the testing laboratory. As the normal range of T4 levels may vary by testing laboratory, the target T4 levels are based on normal ranges determined for each particular testing laboratory.

Dosing may be single dosage or cumulative (serial dosing), and may be readily determined by one skilled in the art. For instance, treatment of a muscular disorder may comprise a one-time administration of an effective dose of a compound, composition, or combination disclosed herein. As a non-limiting example, an effective dose of a compound, composition, or combination disclosed herein can be administered once to a mammal as a single injection or deposition at or near the site exhibiting a symptom of a muscular disorder or a single oral administration of the compound, composition, or combination. Alternatively, treatment of a muscular disorder may comprise multiple administrations of an effective dose of a compound, composition, or combination disclosed herein carried out over a range of time periods, such as daily, once every few days, weekly, monthly or yearly. As a non-limiting example, a compound, a composition, or a combination disclosed herein may be administered once or twice weekly to a mammal. The timing of administration can vary from mammal to mammal, depending upon such factors as the severity of a mammal's symptoms. For example, an effective dose of a compound, composition, or combination disclosed herein can be administered to a mammal once a month for an indefinite period of time, or until the mammal no longer requires therapy. A person of ordinary skill in the art will recognize that the condition of the mammal can be monitored throughout the course of treatment and that the effective amount of a compound, composition, or combination disclosed herein that is administered can be adjusted accordingly.

In other embodiments, the method may further include measuring the patient's $C_{max}$ of the RXR agonist and adjusting the dose to maintain the patient's $C_{max}$ at an optimal level.

In one embodiment, the RXR agonist is 3,7-dimethyl-6 (S),7(S)-methano,7-[1,1,4,4-tetramethyl-1,2,3,4-tetrahydron-aphth-7-yl]2(E),4(E) heptadienoic acid or salts or esters thereof. In another embodiment, the RXR agonist is TARGRETIN® or salts or esters thereof. In another embodiment, RXR agonist may be may be LG268 (LG100268, LGD268, 2-[1-(3,5,5,8,8-pentamethyl-5,6,7,8-tetrahydro-2-naphthyl)cyclopropyl]pyridine-5-carboxylic acid), or salts or esters thereof.

In some embodiments, the method further includes treating the patient with one or more triglyceride lowering agents.

Non-limiting examples of an muscular disorder that can be treated using a compound, composition, or combination disclosed herein include, but is not limited to, acid maltase deficiency, atony, atrophy, ataxia, Becker Muscular Dystrophy (BMD), cardiac muscle ischemia, cardiac muscle infarction, a cardiomyopathy, carnitine deficiency, carnitine palmitoyltransferase deficiency, central core disease (CCD), centronuclear (myotubular) myopathy, cerebral palsy, compartment syndromes, channelopathies, congenital muscular dystrophy (CMD), corticosteroid myopathy, cramps, dermatomyositis, distal muscular dystrophy, Duchenne muscular dystrophy (DMD), dystrophinopathies, Emery-Dreifuss muscular dystrophy (EDMD), facioscapulohumeral muscular dystrophy (FSHD), fibromyalgia, fibrositis, limb girdle muscular dystrophy (LGMD), McArdle syndrome, muscular dystrophy, muscle fatigue, myasthenia gravis, myofascial pain syndrome, myopathy, myotonia, myotonic muscular dystrophy (DM, type 1 or 2; Steinert's disease), nemaline myopathy, oculopharyngeal muscular dystrophy (OCM), myoglobinuria, paramyotonia congenita (Eulenberg's disease), polymyositis, rhabdomyolysis, sarcoglycanopathies, or spasms. In some embodiments, the myopathy is dermatomyositis, inclusion body myositis, or polymyositis. In certain embodiments, the muscular disorder is due to cancers, HIV/AIDS, COPD, chronic steroid use, fibromyalgia, or skeletal muscle myopathies.

In other embodiments, the combination of rexinoids and thyroid hormones are beneficial by effecting heart muscle protection or regeneration either in vivo, or in vitro for subsequent implantation of myocytes into damaged cardiac muscle.

Also provided herein is a method of treating an muscular disorder, the method comprising of administering to an individual in need thereof a therapeutically effective amount of 3,7-dimethyl-6(S),7(S)-methano,7-[1,1,4,4-tetramethyl-1,2,3,4-tetrahydronaphth-7-yl]2(E),4(E) heptadienoic acid, and a therapeutically acceptable amount of thyroxine; and wherein administration of the combination reduces the severity of the muscular disorder in the individual by slowing or stopping progression, or inducing or hastening repair or regeneration of the affected muscle or muscles.

Non-limiting examples of a symptom ameliorated or reduced by a method of treating an muscular disorder disclosed herein include, but is not limited to, weakness, fatigue, stiffness, pain, cramps, ataxia, loss of muscle bulk, exercise intolerance, facial erythema, malaise, metabolism deficiencies, dysphagia, disphonia, rash, periungual hyperemia, telangiectasis, subcutaneous nodules and calcification, ulcerations, lesions, and ptosis.

In some embodiments, the method may be used to treat muscular dystrophy. Muscular dystrophy is a group of hereditary disease with the progressive deterioration and weakening of a patient's muscles and loss of muscle mass. Diagnosis of muscular dystrophy is determined through physical exam, evaluation of the patient's medical history, blood tests (testing for levels of serum creatinine kinase, serum aldolase, aspartate aminotransferase (AST), lactate dehydrogenase (LDH), and myoglobin), muscle biopsies, exercise assessments, genetic, neurological, heart, lung, and imaging testing.

In some embodiments, the method may be used to ameliorate or reduce a symptom of muscular dystrophy. Symptoms of muscular dystrophy may include, but are not limited to, limited or delayed development of motor skills, weak muscles, muscle cramps, ptosis, dysphagia, disphonia, vision problems, and drooling. In other embodiments, the method may treat or reduce complications associated with muscular dystrophy. Complications associated with muscular dystrophy may include, but are not limited to, cardiomyopathy with heart failure, cataracts, decreased movement, depression, lung failure, contractures, mental impairment, and scoliosis.

In some embodiments, the method may reduce the patient's serum aldolase level. In other embodiments, the method may reduce the patient's aldolase level to between about 3.0 Sibley-Lehninger units/dL and about 8.0 Sibley-Lehninger units/dL, or between about 3.0 Sibley-Lehninger units/dL and about 9.0 Sibley-Lehninger units/dL, or between about 20 mU/L and about 60 mU/L.

In other embodiments the method may reduce the patient's serum creatinine level. In other embodiments, the method may reduce the patient's serum creatinine level to between about 5 IU/L and about 100 IU/L for males and between about 10 IU/L and about 70 IU/L for women.

In some embodiments, the method may reduce the patient's AST level. In other embodiments, the method may reduce the patient's AST level to between about 5 IU/L and about 35 IU/L or between about 5 IU/L and about 40 IU/L.

In some embodiments, the method may reduce the patient's LDH level. In other embodiments, the method may reduce the patient's LDH level to between about 290 U/L and about 775 U/L for patients between 0 days old and about 4 days old; between about 545 U/L and about 2000 U/L for patients between about 4 days old to about 10 days old; between about 180 U/L and about 430 U/L for patients between about 10 days old to about 24 months old; between about 110 U/L and about 295 U/L for patients about 24 months old to about 12 years old; between about 100 U/L and about 190 U/L for patients about 12 years old to about 60 years old; or between about 110 U/L and about 210 U/L for patients about 60 years old or older.

In some embodiments, the method may reduce the patient's myoglobin level. In other embodiments, the method may reduce the patient's myoglobin level to between about 0 ng/mL and about 85 ng/mL.

In some embodiments, the method may reduce the patient's creatinine phosphokinase (CPK) levels. In some embodiments, the method may reduce the patient's CPK level to between about 22 U/L and about 198 U/L.

In some embodiments, the ventricular ejection fraction is measured. The ventricular ejection fraction is a reflection of cardiac health and is determined by echocardiography, nuclear stress test, CAT scan, cardiac catheterization, or radionuclide ventriculography (or radionuclide angiography; MUGA). In some embodiments, the ventricular ejection fraction is normalized to between 50 and 70 as a result of the disclosed methods.

A compound, composition, or combination disclosed herein as disclosed herein can also be administered to a mammal in combination with other therapeutic compounds to increase the overall therapeutic effect of the treatment. The use of multiple compounds to treat an indication can increase the beneficial effects while reducing the presence of side effects.

Aspects of the present specification may also be described as follows:

EXAMPLES

The following non-limiting examples are provided for illustrative purposes only in order to facilitate a more complete understanding of representative embodiments now contemplated. These examples should not be construed to limit any of the embodiments described in the present specification, including those pertaining to the methods of treating a muscular disorder using a RXR agonist disclosed herein, in combination with a thyroid hormone, uses of a RXR agonist disclosed herein and a thyroid hormone to manufacture a medicament to treat a muscular disorder.

Example 1

Selective RXR Agonist, IRX4204, Exerts its Biological Effects Through RXR Signaling To determine whether a RXR agonist can mediate its effects via RXRα receptor homodimers, RXRβ receptor homodimers, RXRγ receptor homodimers, or any combination thereof, or the corresponding RAR/RXR heterodimers, receptor-mediated transactivation assays were performed. For transactivation assays assessing RXR homodimer signaling, CV-1 cells were transfected with 1) an expression construct including a full length RXRα, RXRβ, or RXRγ; and 2) a rCRBPII/RXRE-tk-Luc reporter construct that included RXR homodimer-specific RXRE/DR1 responsive element linked to a luciferase gene. For transactivation assays assessing RAR/RXR heterodimer signaling, CV-1 cells were transfected with 1) an expression construct comprising a fusion protein including an estrogen receptor (ER) DNA binding domain linked to the ligand binding domain of RARα, RARβ, or RARγ and 2) a ERE-tk-Luc reporter construct that included an estrogen receptor responsive element linked to a luciferase gene. The ER-RAR fusion proteins provided an accurate readout of only the transfected ER-RAR. After transfection, CV-1 cells were treated with RXR agonist IRX4204 at increasing concentrations for 20 hours before measuring luciferase activity. Luciferase activity is expressed as percent of maximal activity obtained using 1 μM RXR agonist IRX4204 for RXRs and 1 μM all-trans-retinoic acid (ATRA) for RARs (Table 1). Data are mean values±SE from five independent experiments.

pathway. Also, using appropriate receptor and reporter constructs, RXR agonist IRX4204 was shown not to transactivate so called "permissive RXR heterodimers" PPAR/RXR, FXR/RXR and LXR/RXR (FIGS. 1A-C). In this regard, RXR agonist IRX4204 is distinct from other RXR agonists. Additionally, IRX4204 selectively activates the Nurr1/RXR permissive heterodimer (FIG. 1D). Thus, RXR agonist IRX4204 has a unique profile in that it selectively activates only RXR homodimers and Nurr1/RXR heterodimers.

Example 2

Binding Affinity of RXR Agonists

In order to determine the binding affinity for a RXR agonist, competitive displacement assays were performed. RXRα, RXRβ, RXRγ, RARα, RARβ, or RARγ were expressed in SF21 cells using a baculovirus expression system and the resulting proteins were purified. To determine the binding affinity for a RXR agonist for an RXR, purified RXRα, RXRβ, and RXRγ were separately incubated with 10 nM [$^3$H]-9CRA, and the binding affinity of the RXR agonist IRX4204 was determined by competitive displacement of [$^3$H]-9CRA from the receptor. To determine the binding affinity for a RXR agonist for an RAR, purified RARα, RARβ, and RARγ were incubated with 5 nM [$^3$H]-ATRA, and the binding affinity of the RXR agonist IRX4204

TABLE 1

RXR Agonist Potencies in Activating RXRs and RARs

| Compound | Structure | $EC_{50}$ (nM) Efficacy (% of 1 μM IRX4204) | | | $EC_{50}$ (nM) Efficacy (% of 1 μM ATRA) | | |
| --- | --- | --- | --- | --- | --- | --- | --- |
| | | RXRα | RXRβ | RXRγ | RARα | RARβ | RARγ |
| IRX4204 | [structure] | 0.08 ± 0.01 100 | 0.47 ± 0.05 100 | 0.09 ± 0.01 100 | >1,000 | >1,000 | >1,000 |

These results indicate that RXR agonist IRX4204 activated RXR receptors with very high potency ($EC_{50}$<0.5 nM) for all three RXR subtypes (Table 1). In contrast, $EC_{50}$ of the RXR agonist for RARs was >1,000 nM with minimal activity detected at ≥1 μM. This difference represents >2,000-fold selectivity for RXRs over RARs in functional transactivation assays. Additionally, these data demonstrate that RXR agonist IRX4204 was more than 1,000-fold more potent in activating RXR receptors rather than RAR receptors. These results indicate that the biological effects of selective agonists such as IRX4204 are mediated through a RXR signaling pathway and not via a RAR signaling was determined by competitive displacement of [$^3$H]-ATRA from the receptor. Ki values are mean values of at least two independent experiments (Table 2). Standard errors (±) among independent experiments are indicated.

As shown in Table 2, RXR agonist IRX4204 displayed high affinity for RXRα, RXRβ, and RXRγ with Ki values being 1.7, 16, and 43 nM, respectively. In contrast, the RXR agonist IRX4204 bound with very low affinity to each of the RARs (Ki values being >1,000 nM). These data indicate that IRX4204 is highly selective for the RXRs relative to the RARs.

TABLE 2

RXR Agonist Binding Affinities

| Compound | Structure | RXR Binding Affinity Ki (nM) | | | RAR Binding Affinity Ki (nM) | | |
|---|---|---|---|---|---|---|---|
| | | RXRα | RXRβ | RXRγ | RARα | RARβ | RARγ |
| IRX4204 | (structure) | 1.7 ± 0.1 | 16 ± 1.0 | 43 ± 3.0 | 6344 ± 674 | 7552 ± 638 | 4742 ± 405 |

Example 3

Figure 2A:
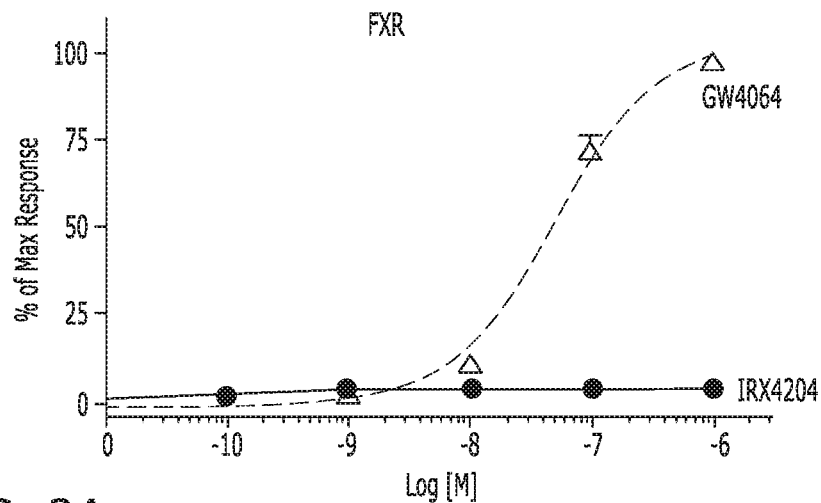
FIGS. 2A-D shows that IRX4204 selectively activates RXR-Nurr1 heterodimers. Transactivation assay of IRX4204 (194204, Formula III) for farnesoid X receptor FXR (FIG. 2A); for liver X receptors LXRα and LXRβ (FIG. 2B); for peroxisome proliferator-activated receptor PPARγ (FIG. 2C); and for Nurr1 receptor in the presence or absence of RXR (FIG. 2D).
Figure 2B:
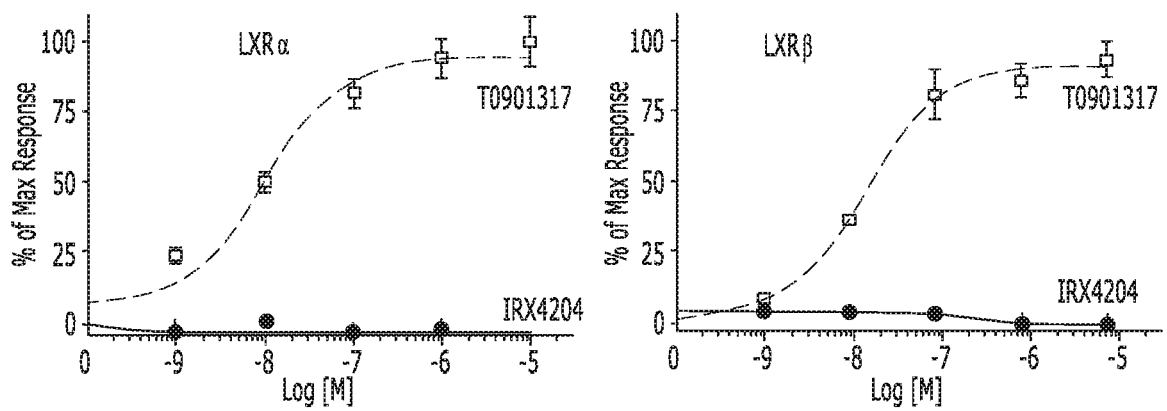
Figure 2C:
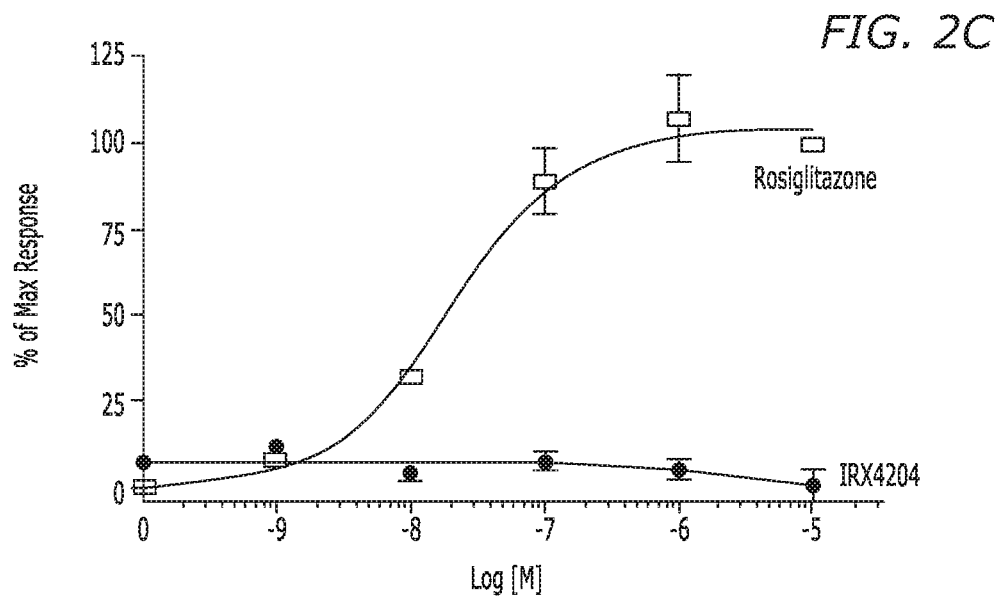
Figure 2D:
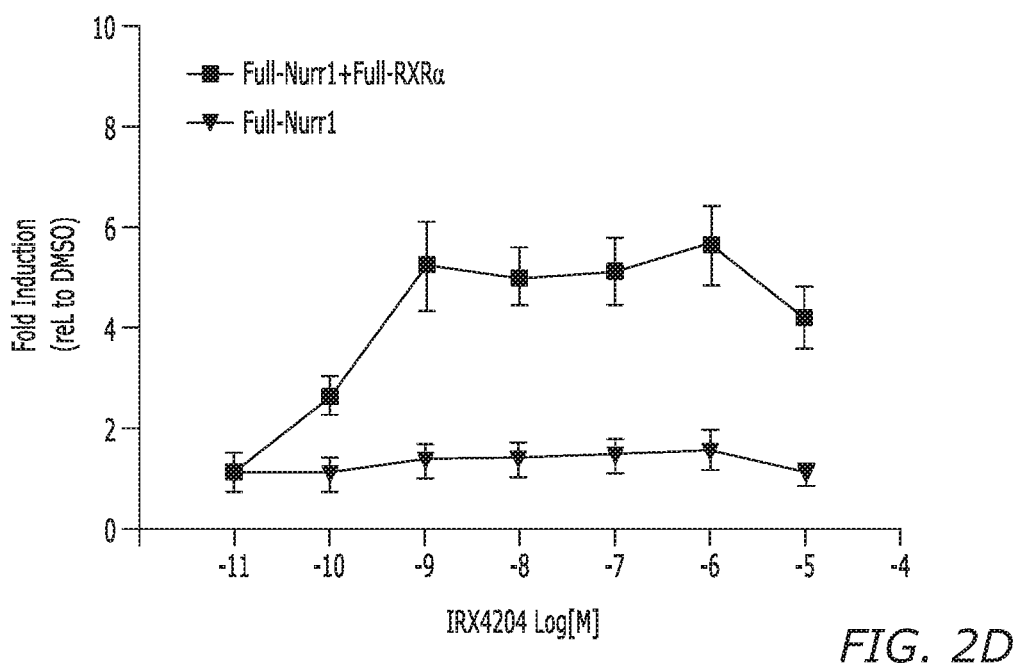

RXR Agonist IRX4204 as a Selective Activator of Nurr1/RXR Permissive Heterodimer In order to determine which permissive RXR heterodimer is activated by the RXR agonist IRX4204, receptor transactivation assays were carried out as follows for PPARγ/RXR, FXR/RXR, LXRα/RXR, LXRβ/RXR, and Nurr1/RXR. For PPARγ: CV-1 cells were transfected with 3x(rAOX/DR1)-tk-Luc reporter gene and an expression vector for PPARγ. For FXR:CV-1 cells were transfected with 3x(IBABP/IRI)-tk-Luc reporter gene and vectors for FXR and RXRα. For LXR:CV-1 cells were transfected with 3x(PLTP/LXRE)-tk-Luc reporter gene with vectors for LXRα or LXRβ. For Nurr1: COS7 cells were transfected with 3xNBRE-tk-luc reporter gene and full length Nurr-1 with or without full-length RXRα plasmid. Cells were then treated with vehicle or IRX4204 for 20 hr. Luciferase data were normalized to co-transfected β-gal activity. Luciferase activity was expressed as percent of maximal activity obtained using specific agonists. Rosiglitazone (PPARγ), GW4064 (FXR), T0901317 (LXR). The data indicate that IRX4204 does not activate FXR/RXR (FIG. 2A), LXRα/RXR or LXRβ/RXR (FIG. 2B), or PPARγ/RXR (FIG. 2C). In contrast, IRX4204 potently ($EC_{50}$<1 nM) activates the Nurr1/RXR heterodimer (FIG. 2D). These data collectively indicate that IRX4204 is a unique RXR agonist in that it selectively activates the Nurr1/RXR heterodimer but not the PPARγ/RXR, FXR/RXR or LXR/RXR heterodimers.

Example 4

Effect of RXR Agonists on Oligodendrocyte Precursor Cell Differentiation

Figure 3:
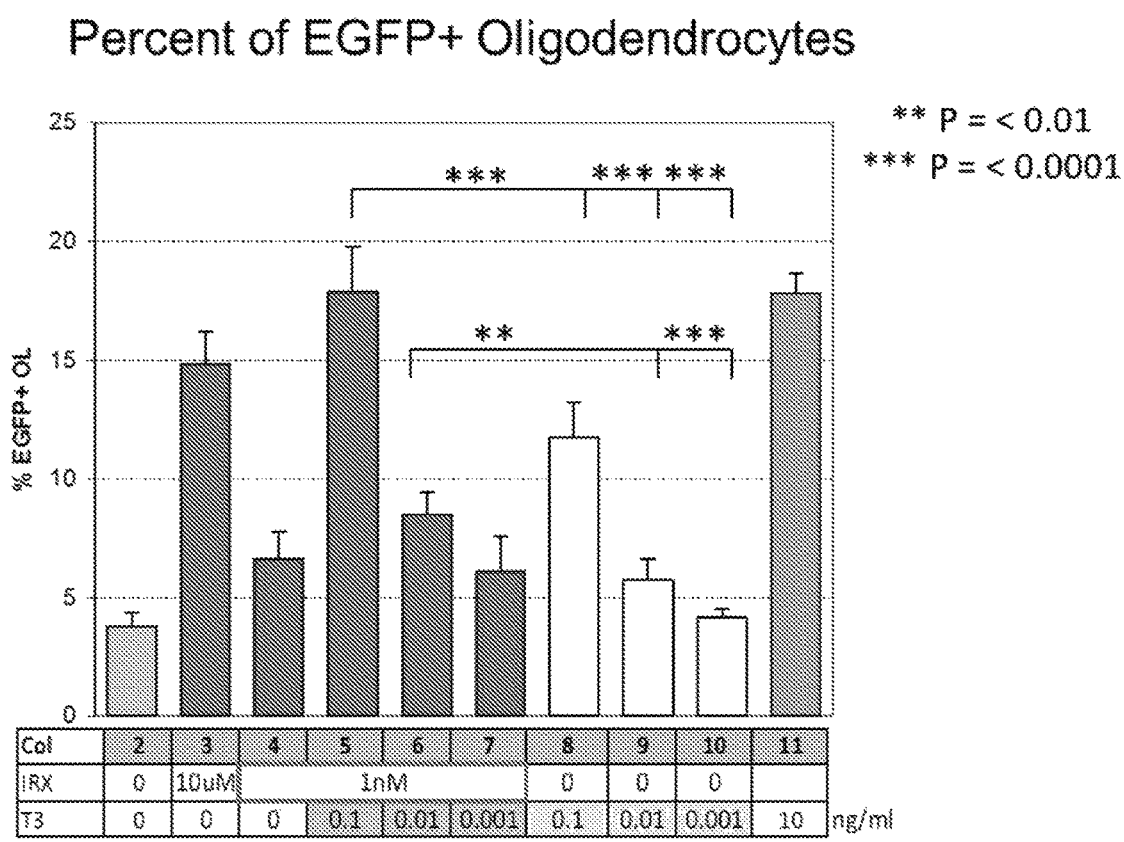
FIG. 3 shows the percentage of green fluorescent protein (EGFP) positive oligodendrocytes after culture of oligodendrocyte precursor cells derived from embryonic mouse brains with IRX4204 and thyroid hormone.

The goal of this study was to evaluate the effect of IRX4204 on differentiation of oligodendrocyte precursor cells (OPCs) into oligodendrocytes. OPCs were generated from a neurosphere culture of E14.5 PLP-EGFP (on C57BL/6J background) mouse brains. The isolated OPCs were treated with IRX4204 and/or T3 to evaluate the expression of green fluorescent protein (EGFP), which correlates with differentiation of OPCs into oligodendrocytes. The EGFP expressing cells were quantified with Cellomics Neuronal Profiling Algorithm. The positive (T3) control demonstrated differentiation of OPCs as expected. The results demonstrate that IRX4204 promotes OPC differentiation into oligodendrocytes as shown by the increase in the number of the EGFP positive cells compared to negative control (DMSO). All tested concentrations showed a significant increase in OPC differentiation into oligodendrocytes (FIG. 3). However, addition of T3 to the IRX4204-treated cultures induced even higher levels of EGFP+ oligodendrocytes demonstrating the significant benefit of the combination of IRX4204 and thyroid hormone.

The EGFP expressing cells in controls and all compounds were quantified with Cellomics Neuronal Profiling Algorithm. The experiment was successful as demonstrated by the significant increase in % EGFP cells in positive control (T3; 8.5%) compared to the negative control (DMSO 2.3%). IRX4204 promotes OPC differentiation into oligodendrocytes as demonstrated by the dose dependent increase in the number of the EGFP positive cells compared to negative control (DMSO). IRX4204 did not show any differences in total cell number and pyknotic cells compared to controls. The results from this study demonstrate that IRX4204 promotes OPC differentiation. The data show a dose-dependent increase in the percentage of EGFP cells compared to the negative control. These date indicate that IRX4204 promotes the growth of myelin-forming cells in cell culture.

Example 5

Mouse Oligodendrocyte Progenitor Cell Differentiation

The purpose of this study was to assess possible effects of IRX4204 in combination with triiodothyronine (T3), on differentiation of mouse oligodendrocyte progenitor cells (OPCs) into oligodendrocytes. OPCs were derived from plp-EGFP expressing mice.

Therapeutic agents were tested in 96-well plates (6 wells per concentration). Negative and positive controls (DMSO or 10 ng/ml T3 thyroid hormone) were included in each plate. All media contained 0.1% DMSO. At the end of the 5-day treatment, cells were imaged on Cellomics in two channels and algorithms were used to count nuclei and EGFP+ oligodendrocytes.

Figure 5:
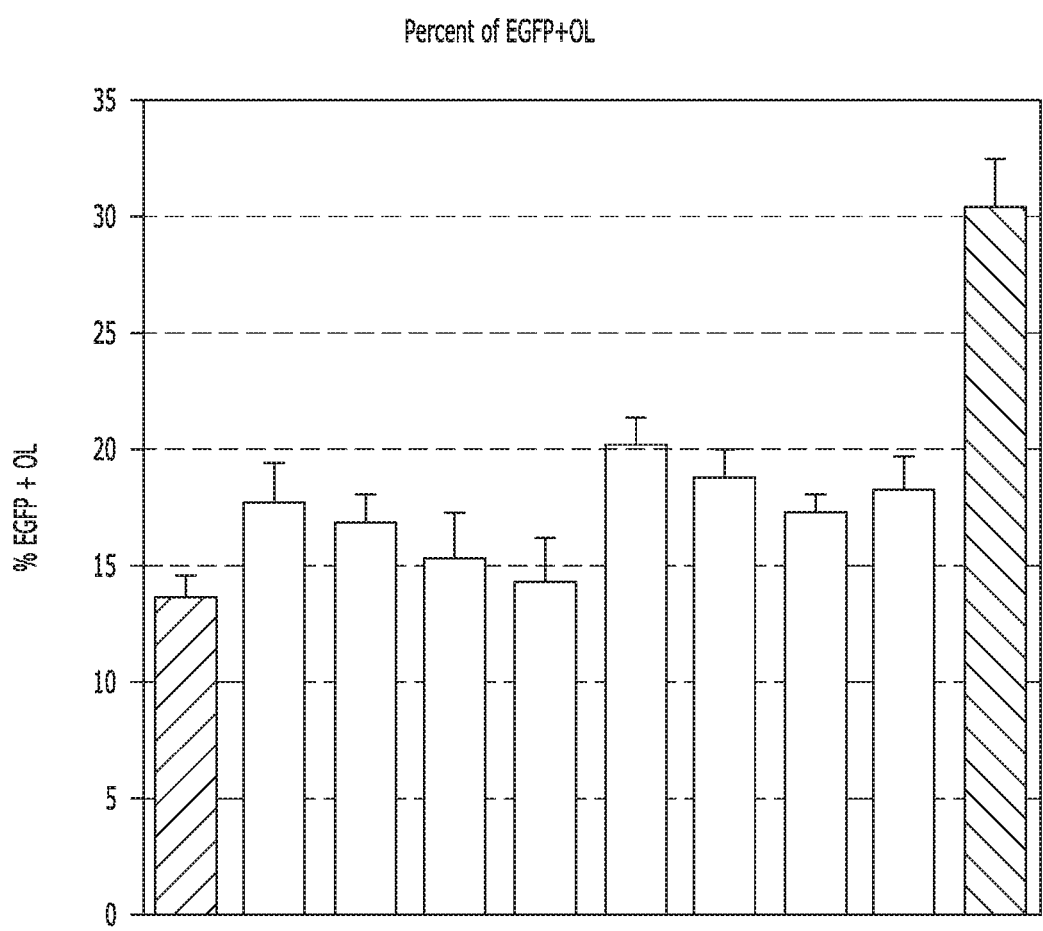
FIG. 5 depicts the percent and fold change of EGFP+ oligodendrocytes following treatment of oligodendrocytes with IRX4204, thyroid hormone, and Vitamin D (*: P<0.05, student's t-test against DMSO control; Error bar, SD).
Figure 6A:
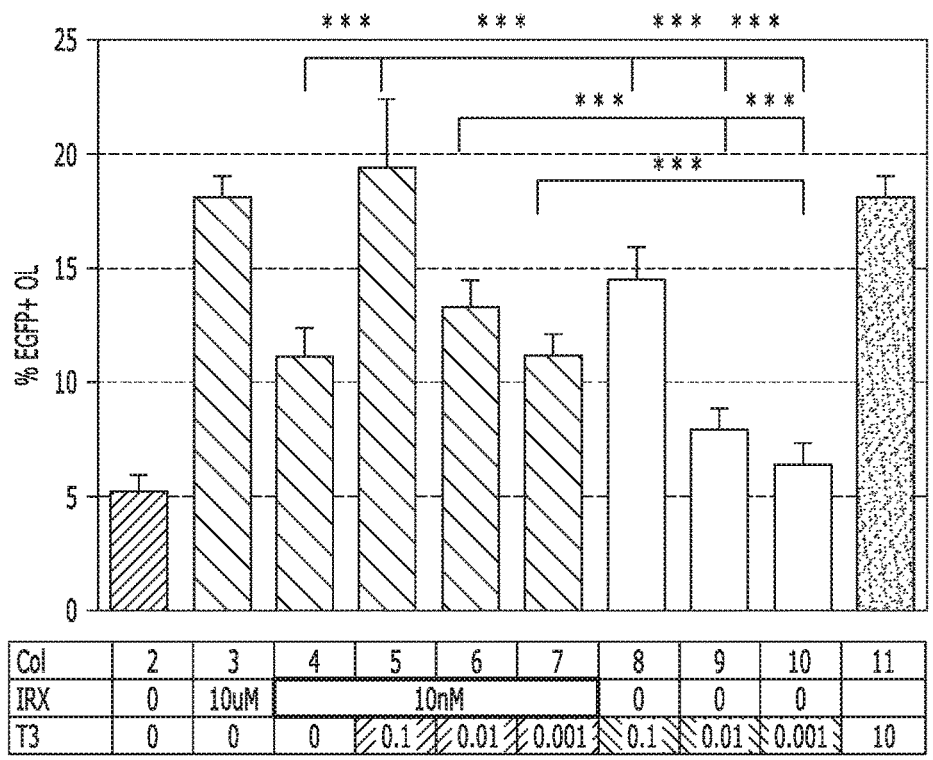
FIGS. 6A-C depicts the percent change of EGFP+ oligodendrocytes following treatment of oligodendrocytes with IRX4204 and thyroid hormone (FIG. 6A: 10 nM IRX4204.
Figure 6B:
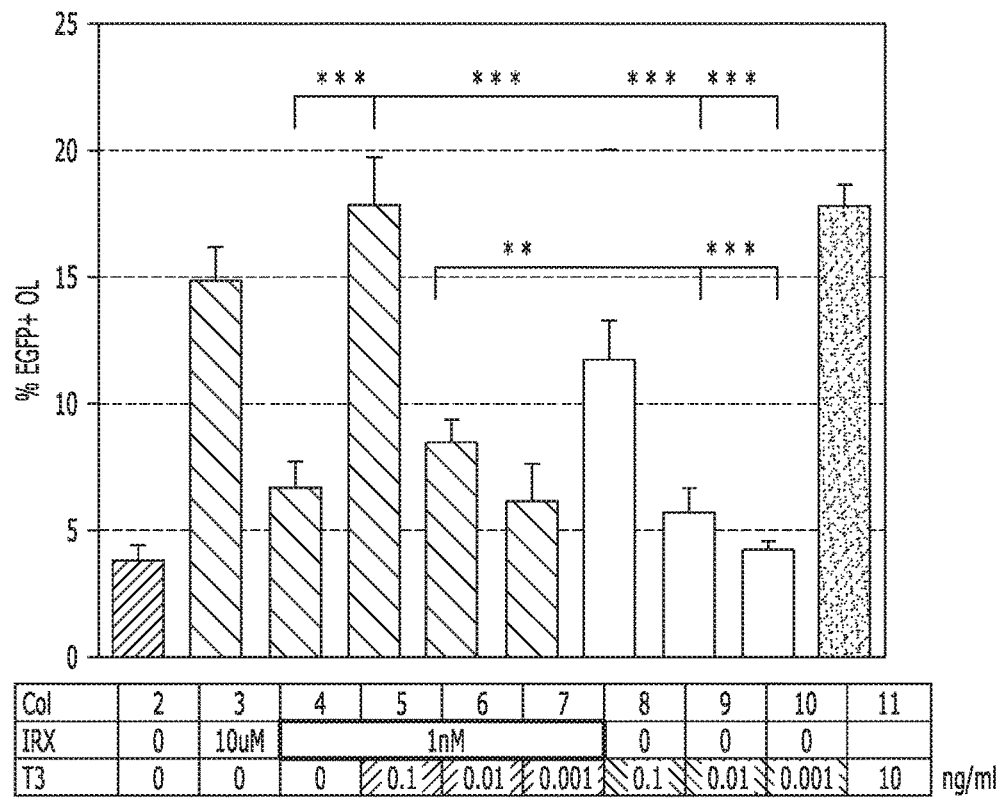
Figure 6C:
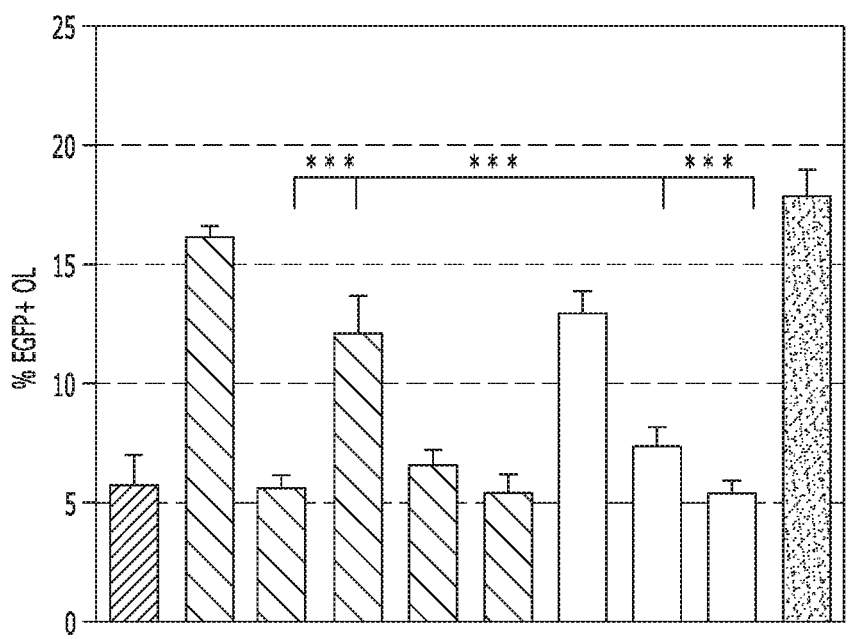

FIG. 5A-C show clear dose-responses in oligodendrocyte production in response to different doses of IRX4204 and T3. The production of oligodendrocytes in response to combination treatments of IRX4204 and T3 was more than that of individual treatment alone in all conditions. This suggests an additive, or potentially a synergistic, effect in driving oligodendrocyte precursor cell differentiation between IRX4204 and T3. Similar results were obtained when cells were stained with MBP antibody and quantified (data not shown). These data suggest that a combination of IRX4204 and T3 (or T4) will be optimal in remyelination.

Example 6

Figure 7:
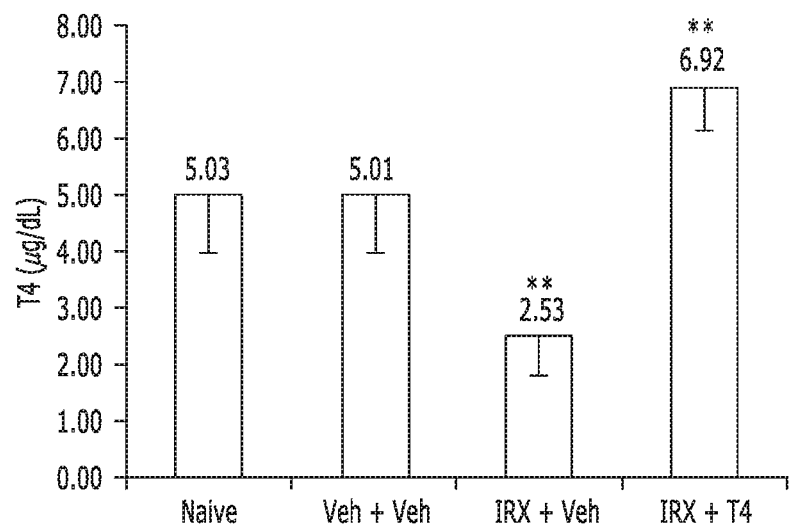
FIG. 7 depicts terminal circulating serum T4 levels in animals that received vehicle, IRX4204 or IRX4204 and T4 (** P<0.005 vs Vehicle and Naïve control).
Figure 8:
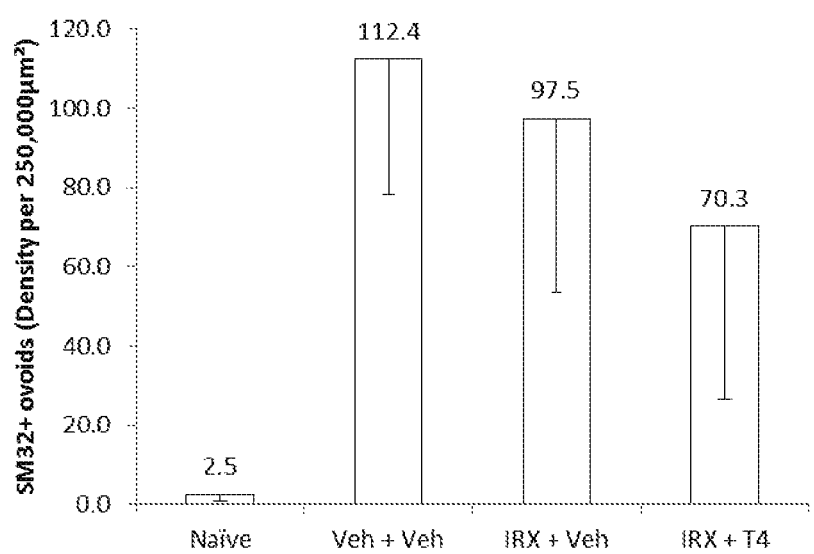
FIG. 8 depicts a quantification of SMI32 positive ovoids in corpus callosum in animals that received vehicle, IRX4204 or IRX4204 and T4 for 6 weeks (* P<0.05 vs Veh+Veh Control).

Evaluation of the Neuroprotective Potential of IRX4204 and IRX4204+Thyroxine in a Mouse Model of Non-Immune Mediated Demyelination The modified cuprizone model (cuprizone+rapamycin) facilitates reliable, reproducible and unequivocal analysis of neurodegeneration caused by demyelination. SMI-32 immunostaining enables the visualization and quantification of swollen and transected axons (ovoids) in the corpus callosum and enables the assessment of the extent of axonal degeneration. There were four groups of mice in the study: cuprizone+rapamycin (CR) only (n=6), CR+vehicles (n=12), CR+IRX4204 (n=12), and CR+IRX4204+thyroxine (n=12). The test articles were administered concurrently with CR for 6 weeks. IRX4204 was administered orally once daily at 10 mg/kg body weight. Thyroxine (T4) treatment was initiated one day after initiation of the IRX4204 treatment. T4 was administered subcutaneously (SC) once daily at 20 ng/g body weight. The CR+vehicles group received the IRX4204 vehicle (oral) and the T4 vehicle (SC). All animals were subjected to terminal blood collection to determine plasma T4 levels. After sacrifice, the density of SMI-32 positive ovoids per unit area was determined for each group. The higher the SMI-32 positive ovoid density, the greater the extent of axonal degeneration. There was a 13.3% reduction in SMI-32+ovoids in the IRX4204 group relative to the vehicles group indicating some neuroprotection by IRX4204 alone. However, the IRX4204+thyroxine group gave a 37.5% reduction relative to the vehicles group indicating that the IRX4204 plus thyroxine combination provides a substantial degree of neuroprotection from the CR-induced neurotoxicity by inhibition of axonal transection in the corpus callosum (FIG. 7).

Example 7

Neuroprotective Effect of IRX4204 in a Mouse Model of Demyelination

The goal of this study was to evaluate the neuroprotective effect of IRX4204 in a mouse model of non-immune mediated demyelination.

In this study, the 6-week demyelination model was used to assess neuroprotective potential of IRX4204 following 6-week concurrent treatment during demyelination. A subgroup of animals were treated with T4 along with IRX4204. The results from this study demonstrate that IRX4204 promotes neuroprotection without reducing the extent of demyelination in the corpus callosum.

Animals (8 week-old male C57BL/6J mice) were subjected to cuprizone diet plus rapamycin injections (CR) for 6 weeks to induce demyelination. Animals were treated with either vehicle or IRX4204 (10 mg/kg, PO), or IRX4204+T4 (10 mg/kg, PO, and 20 ng/g, SQ) daily for the entire 6 weeks during demyelination. All animals were sacrificed after 6 weeks of CR to evaluate axonal integrity and microglial/macrophage activity in the white matter (corpus callosum, CC). Two groups (Vehicle and IRX4204+T4) were further examined for any protective effects on the extent of myelination in the CC.

There was a significant reduction in axonal transection as shown by the decrease in the number of SM132 positive axonal ovoids in the animals treated with IRX4204+T4. However, there was no difference in microglial/macrophage activation and the number of myelinated axons in the CC between the Vehicle and IRX4204+T4 groups. These findings support a neuroprotective role of IRX4204 mediated by a potential direct effect on demyelinated axons.

A total of 50 animals were included in the study, where 43 animals received CR demyelination for 6 weeks. During demyelination, a subset (n=7) of animals were kept on normal diet to serve as naïve age-matched controls. The remaining animals received IRX4204 (n=14) or vehicle (n=14) or IRX4204+T4 (n=15) for 6 weeks concurrently during CR. There was no mortality during the in-life phase. In addition, there were no observed health concerns during the treatment phase. All animals were alert and demonstrated proper grooming behavior. ANOVA analysis with multiple group comparison showed no significant difference in terminal body weights between IRX4204 or vehicle groups.

To assess thyroid hormone levels, terminal blood draws were taken to quantify the levels of T4. Animals treated with IRX4204 alone showed an approximate 50% decrease in T4 levels when compared to vehicle control animals. Exogenous treatment with T4 corrected the thyroid hormone levels as shown by increase in T4 levels in IRX4204+T4 group.

The floating brain sections were immunostained with SMI-32 to visualize and quantify axonal ovoids in the CC. Animals that were subjected to CR showed significantly higher numbers of SM132 stained axonal ovoids in CC compared to naïve animals. There was a significant decrease in the number of axonal ovoids in animals treated with both IRX4204 and T4 compared to Vehicle. IRX4204 alone showed a trend towards decreased number of axonal ovoids but was not statistically different from the Vehicle.

The floating brain sections were immunostained with lba-1 to visualize and quantify microglia/macrophages in CC. Animals subjected to CR and treated with Vehicle had a robust increase in lba1 staining in CC compared to naïve animals. There was no difference in the levels of lba1 staining in IRX4204 or IRX4204+T4 treated animals compared to vehicle.

Semi-thin (1 µm) sections of Epon-embedded CC tissue from animals that received CR and Vehicle or IRX4204+T4 were used to visualize and quantify the number and density of myelinated axons in the CC. Animals that received CR and vehicle demonstrated robust demyelination of the CC. There was no significant difference in the number and density of myelinated axons in IRX4204+T4 treated animals when compared to vehicle.

IRX4204 treatment alone without T4 showed a trend towards decrease in axonal ovoids, but it was statistically not different from vehicle. However, when animals that received IRX4204 were supplemented with exogenous T4 there was a significant decrease in the number of axonal ovoids compared to vehicle. This data along with our previous in vivo findings support a neuroprotective effect of IRX4204. While there was a decrease in axonal ovoids, there was no significant difference in microglial/macrophage activation and myelination in the corpus callosum in Vehicle and IRX4204+T4 groups.

The finding that IRX4204 demonstrated a neuroprotective effect only in the group with supplemental T4 suggests an enhanced effect of the combination therapy over IRX4204 alone.

Figure 9A:
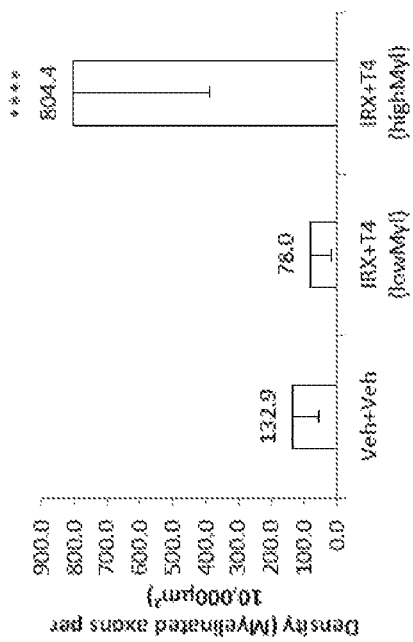
FIGS. 9A-C depicts a quantification of myelination of the corpus callosum following in vivo treatment with combinations described herein, and a separation of the data into potential responders and non-responders (one way ANOVA with Tukey's multiple comparisons, *P<0.05  P<0.01, ** P<0.001).
Figure 9C:
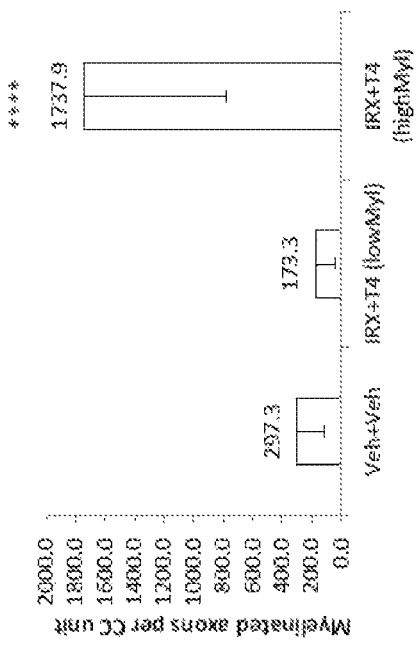
Figure 9B:
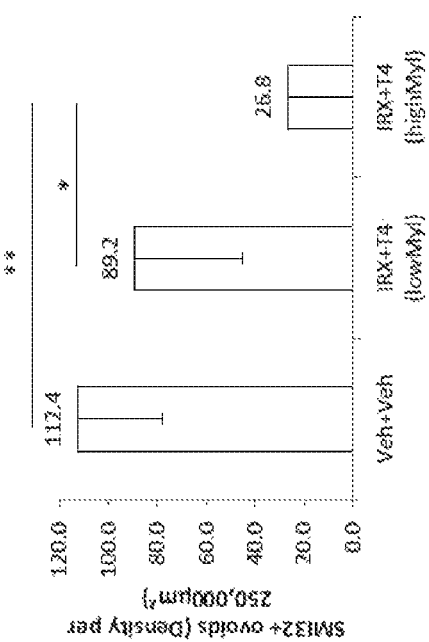

Quantification of myelinated axons in the corpus callosum shows potential responders and non-responders. FIG. 9A-C shows a high correlation between the number of axonal ovoids and myelinated axons (i.e. the animals that had very few ovoids had very high number and density of myelinated axons in the corpus callosum).

Example 8

Effect of IRX4204 in Parkinson's Disease Model

The purpose of this study was to evaluate IRX4204 treatment for amelioration of behavioral deficits in the rat 6-OHDA induced Parkinson Disease (PD) model. The rat model of PD was produced by unilateral intra striatum injection of the neurotoxin 6-hydroxydopamine (6-OHDA). This injection produces dopaminergic (DA) neuron loss on the injected side while sparing the contralateral DA neurons. The study design is depicted in Table 3.

TABLE 3

| Group # | Group Size | Test Item | Route | Dose Level of Test Item (mg/kg) | Dose Volume of Test Item (ml/kg) | Dosing Regimen | Testing Regimen |
|---|---|---|---|---|---|---|---|
| 1 | n = 13 | Vehicle TA1 | PO | NA | 5 | Once daily from day 4 until the end of the study (day 24) | Paw Placement/cylinder test: Day −1 (baseline), 3, 10, 17, and 24. |
|  |  | Vehicle TA2 | SC |  | 1 |  |  |
| 2 | n = 13 | TA1 | PO | 10 | 5 |  |  |
|  |  | Vehicle TA2 | SC | NA | 1 |  |  |
| 3 | n = 13 | Vehicle TA1 | PO | NA | 5 |  |  |
|  |  | TA2 | SC | T3: 1.5 μg/kg T4: 9 μg/kg | 1 |  |  |
| 4 | n = 12 | TA1 | PO | 10 | 5 |  |  |
|  |  | TA2 | SC | T3: 1.5 μg/kg T4: 9 μg/kg | 1 |  |  |

The paw placement (cylinder test) was used for assessment of the damage. This test assessed a rat's independent forelimb use to support the body against the walls of a cylindrical enclosure. The test took advantage of the animals' innate drive to explore a novel environment by standing on the hind limbs and leaning towards the enclosing walls.

To perform this test, rats were placed individually in a glass cylinder (21 cm diameter, 34 cm height) and wall exploration was recorded for 3 minutes. No habituation to the cylinder prior to recording was allowed.

The statistical analysis was performed as ratio between the intact and impaired legs (R/L ratio). The ratio was expressed as the values of intact right +both forelimbs divided by the values of impaired left +both forelimbs. A lower value of the ratio means greater healing of the 6-OHDA induced brain damage.

All treated animals gained weight throughout the study. The mean body weight of animals treated with the test item IRX4204 (TA1) with the vehicle of TA2 (group 2) or in combination with thyroxine and triiodothyronine (TA2; group 4) were significantly higher than the vehicle treated group (Group 1) on study days 17 and 24 (157.17±2.93% for Group 2 and 157.61±3.54% for Group 4 vs. 142.62±2.93% for the Vehicle group on day 24; $p<0.05$).

All animals with R/L ratio>1.5 were included in the study (ratio between the intact (R) and impaired legs (L) was expressed as the values of intact right +both forelimbs divided into the values of impaired left +both forelimbs).

Paw placement was measured prior to induction of lesion (baseline) and again 3 days after 6-OHDA injection, which was one day prior to IRX4204 treatment. Once a week during three weeks (study days 10, 17 and 24), the animals were re-tested for their performance in the paw placement test.

Animals were pre-selected based on the R/L ratio on study day 3, when the averaged ratio between the injured side and the intact side was increased relative to baseline levels (1.01±0.01 prior to surgery vs. 6.49±0.59, 3 days after surgery).

Figure 4:
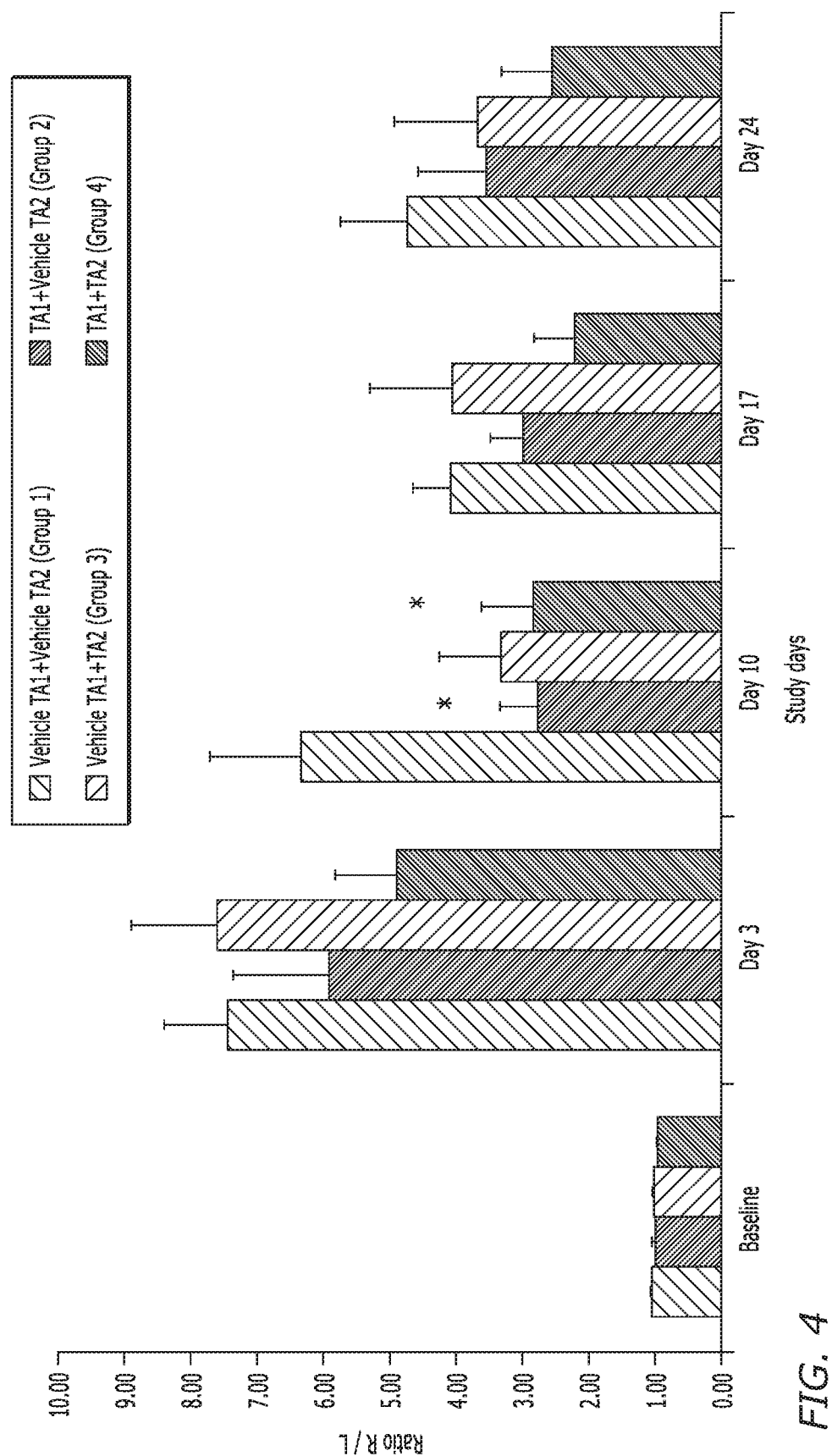
FIG. 4 depicts changes in paw placement behavior in a rat 6-OHDA induced Parkinson Disease upon treatment with compounds and combinations described herein (*p<0.05 vs. vehicle using one way ANOVA followed by Dunnett test).

As shown in FIG. 4, treatment with IRX4204 (TA1) with the vehicle of TA2 (group 2) or in combination with thyroxine and triiodothyronine (TA2; group 4) significantly reduced the mean calculated R/L ratio, compared to the vehicle treated group (group 1) on study day 10 (2.76±0.57 for Group 2 and 2.86±0.76 for Group 4 vs. 6.33±1.41 for the Vehicle group; $p<0.05$).

The mean calculated ratio was lower in these groups compared to the vehicle group also on study days 17 and 24, however this ratio was not statistically significant.

The average value of the ratio was calculated from the four values from days 3, 10, 17 and 24. The calculated values for group 2 and group 4 are 3.79 and 3.14, respectively. This indicates that group 4 (IRX4204 in combination with thyroxine and triiodothyronine) is more effective than group 2 (IRX4204) alone.

Example 9

A Human Clinical Trial to Demonstrate Effects of IRX4204 in Parkinson's Disease

An open-label, single site clinical study of early Parkinson's Disease subjects treated with IRX4204 was conducted to determine whether the preclinical promise of IRX4204 as a disease modifying agent for PD will translate to the clinical setting upon treatment of early PD patients with IRX4204 as determined by Unified Parkinson's Disease Rating Scale (UPDRS) measurements and safety assessments. The changes in UPDRS scores were correlated with circulating thyroxine levels.

The objectives of this study were to further characterize the safety and tolerability of IRX4204 in early patients, particularly reduction in T4 levels, and to evaluate the effect of treatment with IRX4204 on the motor symptoms of PD measured by the UPDRS.

The study endpoints were (1) the change in motor testing scores from end of dosing period (Day 17), and (2) changes in T4 levels.

This was a single site, open-label study designed to examine efficacy (reduction in UPDRS scores) and safety of 3 dose levels of IRX4204 in cohorts of early PD patients for a period of approximately two weeks. In the three cohorts, each subject reported to the clinical research site on at least 3 occasions:
Screening (Visit 1)—Screening to determine eligibility (up to 30 days prior to Baseline Visit)
Baseline Period (Visit 2)—Treatment with IRX4204 began on Day 1.
Week 2 (Visit 3)—subjects returned to the clinic approximately 17 days after initiation of IRX4204 for safety and efficacy evaluations.

Safety and tolerability was assessed through all study visits including blood and urine samples for laboratory tests, ECGs, physical examination, neurological examination and assessments for adverse events.

To qualify for study participation, subjects were required to meet the following criteria: 40-80 years of age, inclusive; have a clinical diagnosis of PD based on the UK Brain Bank Criteria; participant has Hoehn and Yahr stage<3; participant may be treated with PD symptomatic therapy on a stable dose for at least 30 days prior to the Screening Visit. Dose levels of PD symptomatic therapies will remain stable through the study; must be willing and able to provide informed consent; females must be of either non-child bearing potential or must be willing to avoid pregnancy by using medically accepted contraception for 4 weeks prior to and 4 weeks following the last dose of study medication.

Subjects who met any of the following criteria were not included in the study: has any form of Parkinsonism other than idiopathic PD; are currently experiencing motor fluctuations (end of dose wearing off or dyskinesia) reflective of later stages of PD; has evidence of dementia or significant cognitive dysfunction; has clinically significant abnormal laboratory value and/or clinically significant unstable medical or psychiatric illness; the subject has any disorder that may interfere with drug absorption, distribution, metabolism or excretion; the subject has evidence of clinically significant gastrointestinal, cardiovascular, hepatic, pulmonary, or other disorder or disease; pregnancy or breastfeeding.

The clinical site prepared the study drug for administration by dispensing the correct dosage (20 mg/day, 10 mg/day or 5 mg/day) of IRX4204 for each subject. On Day 1, subjects received their first dose of IRX4204. After Day 1, IRX4204 drug dosing occurred at home daily. Patients took their daily dose of study medication with food approximately the same time each day, preferably between 8 AM and 10 AM. On Day 1, subjects received a 15-day supply of IRX4204 for a once daily dose of 20 mg, 10 mg, or 5 mg. Five subjects were recruited for each of the three dose levels. All fifteen subjects completed 15 days of dosing.

All subjects (n=52 total, n=12-13 per dose level) completed 15 days of dosing and returned to the clinic at the end of 2 weeks (day 15-17) for UPDRS score determination and safety assessments including determination of plasma thyroxine (T4) levels. Percent changes in Total Motor scores, Total UPDRS scores and plasma T4 values were determined according to the following:

$$\text{Percent Change} = \frac{\text{Baseline Value} - 2 \text{ Week Value}}{\text{Baseline Value}} \times 100$$

The average percent changes in Total Motor and Total UPDRS scores for the three dose levels are given in Table 4. A negative score indicates an improvement in the disease as measured by the comprehensive UPDRS evaluation. The largest therapeutic response to IRX4204 treatment as measured by the Total Motor score (−31.4%) was obtained for the lowest dose of IRX4204 (5 mg/day). Surprisingly, there was less efficacy, as measured by the Total Motor sores, at each of the higher doses, 10 mg/day (11.7%) and 20 mg/day (−14.5%). Similar results were obtained when the Total UPDRS scores were considered. The best therapeutic response was obtained with the 5 mg/day cohort (−18.7%). Each of the higher doses, 10 mg/day and 20 mg/day, were progressively less efficacious with total UPDRS changes of −13.6% and 6.6%, respectively.

TABLE 4

| Dose | Total Motor Change | Total UPDRS Change |
|---|---|---|
| 20 mg/day | −14.5% | −6.6% |
| 10 mg/day | −11.7% | −13.6% |
| 5 mg/day | −31.4% | −18.7% |

The average percent changes in plasma T4 levels for the three cohorts are given in Table 5. The relationship between dose level and percentage reduction in plasma thyroxine (T4) was direct: the higher the dose of IRX4204 the greater the decrease in T4 levels. The 20 mg/day dose of IRX4204 leads to an almost complete abrogation of plasma T4 (98.8% reduction). Interestingly, this high dose of IRX4204 is associated with the least efficacy (only a 6.6% reduction in Total UPDRS scores).

TABLE 5

| Dose | Change in TSH |
|---|---|
| 20 mg/day | −98.8% |
| 10 mg/day | −36.6% |
| 5 mg/day | −28.9% |

These data in a human clinical trial clearly indicate that the reduction in thyroid hormone levels upon dosing with IRX4204 negatively impacts the therapeutic benefit of IRX4204. The clinical trial data from shows an inverse relationship between suppression of the thyroid axis (manifested by suppression of TSH, thyroid stimulating hormone) and clinical improvement from baseline in total motor scores and UPDRS.

Example 10

Comparison of Bexarotene, IRX4204, and IRX4204+Thyroxine in Cell Differentiation In order to determine and compare the efficacy of bexarotene, IRX4204, and IRX4204+thyroxine in differentiation of stem cells, stem cells are exposed to increasing concentrations of each compound. Pluripotent P19 cells (ATCC) are grown in culture medium and four days after aggregation are transferred to culture dishes for culture on gelatin-coated cover slips in the presence of varying concentrations of bexarotene, IRX4204, IRX4204+thyroxine, retinoic acid, or vehicle alone ranging in concentrations of approximately 1 nM to about 1 µM in the presence of 1% dimethyl sulfoxide (DMSO).

Cells fixed to cover slips are then incubated with primary antibodies for skeletal muscle markers and then labeled with secondary antibodies. Microscopy analysis is performed and the number of skeletal myocytes quantified. Treatment with IRX4204 or IRX4204+thyroxine show a higher number of myogenically differentiated cells as compared to cells treated with retinoic acid, bexarotene, or vehicle alone; treatment IRX4204 with thyroid hormone shows a higher number of myogenically differentiated cells as compared to cells treated with IRX4204 alone.

To test the potency of RXRs on myogenic conversion of embryonic stem cells (ES), embryoid bodies are formed without DMSO. The embryoid bodies are treated with retinoic acid, bexarotene, IRX4204, IRX4204+thyroxine, or vehicle alone ranging in concentrations of approximately 1 nM to about 1 µM and are plated on cover slips and stained for musculoskeletal markers. Myoblasts are examined through microscopy and the number of myocytes counted. Cells treated with IRX4204 or IRX4204+thyroxine are more potent at increasing differentiation than treatment with retinoic acid, bexarotene, or vehicle alone, and IRX4204+thyroxine is more potent in increasing differentiation than IRX4204 alone.

Example 11

Comparison of IRX4204 and IRX4204+Thyroxine in Myoblast Differentiation

In order to determine and compare the efficacy of IRX4204 and IRX4204+thyroxine in myoblast differentiation, murine skeletal muscle myoblasts and primary myoblasts are cultured. Myogenic differentiation is initiated when cells are approximately 60-80% confluent, with the cells being differentiated into cell types, such as myotubes.

Cells are treated with thyroxine, IRX4204, IRX4204+thyroxine, or vehicle only in concentrations ranging from about 10 nM to about 1 µM. Cells treated with IRX4204 or IRX4204+thyroxine demonstrate increased numbers of microfibers as compared to cells treated with thyroxine or vehicle alone, with cells treated with IRX4204+thyroxine showing a greater number of differentiated cells than cells treated with IRX4204 alone. Thus, IRX4204+thyroxine is more effective in myoblast differentiation then treatment with thyroxine or IRX4204 alone.

Example 12

Effects of Treatment with Bexarotene, IRX4204, or IRX4204+Thyroxine on Cardiac Hypertrophy In order to determine and compare the efficacy of bexarotene, IRX4204, and IRX4204+thyroxine in cardiac hypertrophy, each compound is administered to spontaneously hypertensive rats (SHRs) and the effects monitored. Four weeks old SHRs and control rats are randomized and put into groups of 5-10 rats/group. Each group is administered 10 mg to 100 mg/kg bexarotene, IRX4204, IRX4204a+thyroxine, or vehicle alone. Transthoratic echocardiographs are performed to determine cardiac weights and measurements.

When the animals reach 12 weeks of age, cardiac mass and cardiac wall thickness in the SHRs is significantly increased in vehicle-only treated animals and as compared to the control groups. SHRs treated with bexarotene, IRX4204, or IRX4204+thyroxine show an inhibition of the increase in cardiac mass and wall thickness as compared to vehicle-only treated SHRs. Animals treated with IRX4204 or IRX4204+thyroxine show a greater inhibition of the increase in cardiac mass and wall thickness as compared to bexarotene-treated animals, and animals treated with IRX4204+thyroxine show the greatest inhibition.

The animals are sacrificed at 16 weeks of age to determine cardiac hypertrophy. Hypertrophy is determined by the animal's left ventricle weight to body weight ratio. The myocyte cross-sectional area is also determined. Approximately 10 mg to about 30 mg of the animal's left ventricle is homogenized and subject to sodium dodecyl sulfate polyacrylamide gel electrophoresis (SDS-PAGE) and immunoblot analysis.

SHRs treated with bexarotene, IRX4204, or IRX4204+thyroxine show a significantly lower ratio of left ventricle weight to body weight as compared to vehicle-only treated SHRs. Animals treated with IRX4204 or IRX4204+thyroxine show a lower ratio of left ventricle weight to body weight as compared to bexarotene-treated animals, and animals treated with IRX4204+thyroxine show the lowest ratio of left ventricle weight to body weight.

SHRs treated with vehicle only show a significant increase in cardiomyocyte cross-sectional area as compared to the control animals. Animals treated with IRX4204 or IRX4204+thyroxine show a greater inhibition of cardiomyocyte cross-sectional area increases than treatment with bexarotene, and animals treated with IRX4204+thyroxine show the greatest inhibition of cardiomyocyte cross-sectional area increases. Also, in immunoblot analysis, RXRα expression in cardiac muscle tissue is up-regulated more in animals treated IRX4204 or IRX4204+thyroxine than with bexarotene, and animals treated with IRX4204+thyroxine have a highest upregulation of RXRα than with treatment of IRX4204 alone.

Thus, treatment IRX4204 and IRX4204+thyroxine each show a greater efficacy in treating left ventrical hypertrophy in hypertensive rats than treatment with bexarotene.

In closing, it is to be understood that although aspects of the present specification are highlighted by referring to specific embodiments, one skilled in the art will readily appreciate that these disclosed embodiments are only illustrative of the principles of the subject matter disclosed herein. Therefore, it should be understood that the disclosed subject matter is in no way limited to a particular methodology, protocol, and/or reagent, etc., described herein. As such, various modifications or changes to or alternative configurations of the disclosed subject matter can be made in accordance with the teachings herein without departing from the spirit of the present specification. Lastly, the terminology used herein is for the purpose of describing particular embodiments only, and is not intended to limit the scope of the present invention, which is defined solely by the claims. Accordingly, the present invention is not limited to that precisely as shown and described.

Certain embodiments of the present invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the present invention to be practiced otherwise than specifically described herein. Accordingly, this invention includes all modifications and equivalents of the subject matter recited in the claims appended hereto as permitted by applicable law. Moreover, any combination of the above-described embodiments in all possible variations thereof is encompassed by the invention unless otherwise indicated herein or otherwise clearly contradicted by context.

Groupings of alternative embodiments, elements, or steps of the present invention are not to be construed as limitations. Each group member may be referred to and claimed individually or in any combination with other group members disclosed herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Unless otherwise indicated, all numbers expressing a characteristic, item, quantity, parameter, property, term, and so forth used in the present specification and claims are to be understood as being modified in all instances by the term "about." As used herein, the term "about" means that the characteristic, item, quantity, parameter, property, or term so qualified encompasses a range of plus or minus ten percent above and below the value of the stated characteristic, item, quantity, parameter, property, or term. Accordingly, unless indicated to the contrary, the numerical parameters set forth in the specification and attached claims are approximations that may vary. At the very least, and not as an attempt to limit the application of the doctrine of equivalents to the scope of the claims, each numerical indication should at least be construed in light of the number of reported significant digits and by applying ordinary rounding techniques. Notwithstanding that the numerical ranges and values setting forth the broad scope of the invention are approximations, the numerical ranges and values set forth in the specific examples are reported as precisely as possible. Any numerical range or value, however, inherently contains certain errors necessarily resulting from the standard deviation found in their respective testing measurements. Recitation of numerical ranges of values herein is merely intended to serve as a shorthand method of referring individually to each separate numerical value falling within the range. Unless otherwise indicated herein, each individual value of a numerical range is incorporated into the present specification as if it were individually recited herein.

The terms "a," "an," "the" and similar referents used in the context of describing the present invention (especially in the context of the following claims) are to be construed to cover both the singular and the plural, unless otherwise indicated herein or clearly contradicted by context. All methods described herein can be performed in any suitable order unless otherwise indicated herein or otherwise clearly contradicted by context. The use of any and all examples, or exemplary language (e.g., "such as") provided herein is intended merely to better illuminate the present invention and does not pose a limitation on the scope of the invention otherwise claimed. No language in the present specification should be construed as indicating any non-claimed element essential to the practice of the invention.

Specific embodiments disclosed herein may be further limited in the claims using consisting of or consisting essentially of language. When used in the claims, whether as filed or added per amendment, the transition term "consisting of" excludes any element, step, or ingredient not specified in the claims. The transition term "consisting essentially of" limits the scope of a claim to the specified materials or steps and those that do not materially affect the basic and novel characteristic(s). Embodiments of the present invention so claimed are inherently or expressly described and enabled herein.

All patents, patent publications, and other publications referenced and identified in the present specification are individually and expressly incorporated herein by reference in their entirety for the purpose of describing and disclosing, for example, the compositions and methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

What is claimed is:

1. A method of treating a muscular disorder, the method comprising administering to an individual in need thereof a therapeutically effective amount of a RXR agonist and a thyroid hormone, wherein the RXR agonist has the structure of Formula II

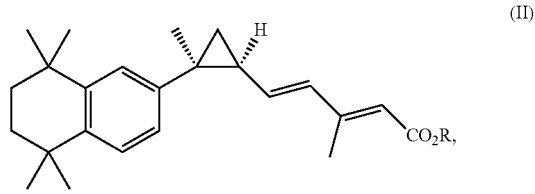

wherein R is H or lower alkyl of 1 to 6 carbon; or a pharmaceutically acceptable salt thereof;

wherein administration of the RXR agonist and the thyroid hormone treats the muscular disorder in the individual more effectively than either the RXR agonist or the thyroid hormone alone; and wherein the muscular disorder is cardiac muscle infarction.

2. The method according to claim 1, wherein is the RXR agonist is a selective RXR agonist comprising 3,7-dimethyl-6(S),7(S)-methano, 7-[1,1,4,4-tetramethyl-1,2,3,4-tetrahydronaphth-7-yl]2(E),4(E) heptadienoic acid.

3. The method according to claim 1, wherein the RXR agonist is 3,7-dimethyl-6(S),7(S)-methano, 7-[1,1,4,4-tetramethyl-1,2,3,4-tetrahydronaphth-7-yl]2(E),4(E) heptadienoic ethyl ester.

4. The method according to claim 1, wherein the thyroid hormone is thyroxine.

5. The method according to claim 1, wherein the therapeutically effective amount of an ester of the RXR agonist having the structure of Formula II is about 0.001 mg/day to about 1000 mg/day.

6. The method according to claim 1, wherein the therapeutically effective amount of the RXR agonist is about 0.001 mg/day to about 1000 mg/day.

7. The method according to claim 1, wherein the therapeutically effective amount of the RXR agonist is about 1 mg/day to about 100 mg/day.

8. The method according to claim 4, wherein the dose of the thyroxine is about 12.5 μg/day to about 250 μg/day.

9. The method according to claim 1, wherein the RXR agonist is administered by nasal administration.

10. The method according to claim 1, wherein the RXR agonist is administered orally.

11. The method according to claim 1, wherein the RXR agonist and the thyroid hormone are both administered substantially simultaneously.

12. The method according to claim 1, wherein the RXR agonist and the thyroid hormone are administered on different schedules.

13. The method according to claim 1, wherein the thyroid hormone is administered orally.

14. The method according to claim 1, wherein the combination of the RXR agonist and the thyroid hormone is beneficial by effecting heart muscle protection or regeneration in vivo.

15. A method of treating a muscular disorder, the method comprising administering to an individual in need thereof a therapeutically effective amount of 3,7-di methyl-6(S),7(S)-methano, 7-[1, 1,4,4-tetramethyl-1,2,3,4-tetrahydronaphth-7-yl]2(E),4(E) heptadienoic acid, and thyroxine; and wherein administration of the combination reduces the severity of the muscular disorder in the individual by slowing or stopping progression, and/or inducing or hastening repair or regeneration of the affected muscle or muscles, wherein administration of the RXR agonist and the thyroxine treats the muscular disorder in the individual more effectively than either the RXR agonist or the thyroxine alone, wherein the muscular disorder is cardiac muscle infarction.

* * * * *